US010213556B2

(12) United States Patent
Young et al.

(10) Patent No.: US 10,213,556 B2
(45) Date of Patent: Feb. 26, 2019

(54) ACCURATE DOSE CONTROL MECHANISMS AND DRUG DELIVERY SYRINGES

(71) Applicant: UNL Holdings LLC, New York, NY (US)

(72) Inventors: Nathaniel Ryan Young, Felton, PA (US); Lou Castagna, Middletown, PA (US); Gary Richardson, York, PA (US); Gautam N. Shetty, Lancaster, PA (US)

(73) Assignee: UNL Holdings LLC, New York, NY (US)

( * ) Notice: Subject to any disclaimer, the term of this patent is extended or adjusted under 35 U.S.C. 154(b) by 85 days.

(21) Appl. No.: 15/163,458

(22) Filed: May 24, 2016

(65) Prior Publication Data
US 2016/0263329 A1 Sep. 15, 2016

Related U.S. Application Data

(63) Continuation-in-part of application No. 13/707,201, filed on Dec. 6, 2012, now Pat. No. 9,345,839.
(Continued)

(51) Int. Cl.
*A61M 5/315* (2006.01)
*A61M 5/28* (2006.01)
*A61M 5/31* (2006.01)

(52) U.S. Cl.
CPC .......... *A61M 5/31526* (2013.01); *A61M 5/28* (2013.01); *A61M 5/31528* (2013.01);
(Continued)

(58) Field of Classification Search
CPC .......... A61M 5/31528; A61M 5/31575; A61M 5/31525
See application file for complete search history.

(56) References Cited

U.S. PATENT DOCUMENTS

| 2,943,624 A | 7/1960 | Alquist |
| 3,596,659 A | 8/1971 | Glasser |

(Continued)

FOREIGN PATENT DOCUMENTS

| AU | 2009217376 A1 | 10/2009 |
| CN | 201168280 Y | 12/2008 |

(Continued)

OTHER PUBLICATIONS

European Patent Office, International Search Report in International Patent Application No. PCT/US2012/068210, dated Apr. 24, 2013, 6 pp.

(Continued)

*Primary Examiner* — Deanna K Hall
(74) *Attorney, Agent, or Firm* — Hamilton, Brook, Smith & Reynolds, P.C.

(57) ABSTRACT

A dose control mechanism for a syringe includes an engaging screw thread arrangement between an exterior surface of a plunger and a longitudinally extending channel of a housing. The engaging screw thread arrangement includes at least one thread segment and a pitch guide including a variable pitch thread. At least a portion of the longitudinally extending channel of the housing including one of the pitch guide and the at least one thread segment, and the plunger includes the other of the pitch guide and the at least one thread segment. The plunger resides at least partially within the housing with the at least one thread segment engaged with the pitch guide. An accurate dose drug delivery syringe includes such a dose control mechanism, a barrel, a plunger seal, and a barrel adapter assembly having a barrel tip and a needle. The syringe may be a fill-at-time-of-use syringe, a pre-filled syringe, or a safety syringe having integrated needle retraction or needle sheathing safety features, or a (Continued)

combination thereof. Methods of assembly, manufacturing, and operation are similarly disclosed.

20 Claims, 24 Drawing Sheets

Related U.S. Application Data

(60) Provisional application No. 61/568,509, filed on Dec. 8, 2011.

(52) U.S. Cl.
CPC . *A61M 5/31575* (2013.01); *A61M 2005/3139* (2013.01); *A61M 2005/3152* (2013.01); *Y10T 29/49826* (2015.01)

(56) References Cited

U.S. PATENT DOCUMENTS

| | | | |
|---|---|---|---|
| 4,018,223 A | 4/1977 | Ethington | |
| 4,444,335 A | 4/1984 | Wood et al. | |
| 4,465,478 A | 8/1984 | Sabelman et al. | |
| 4,687,472 A | 8/1987 | Gross | |
| 4,865,591 A | 9/1989 | Sams | |
| 4,936,833 A | 6/1990 | Sams | |
| 5,019,045 A | 5/1991 | Lee | |
| 5,115,816 A | 5/1992 | Lee | |
| 5,135,511 A | 8/1992 | Houghton et al. | |
| 5,250,030 A | 10/1993 | Corsich | |
| 5,308,322 A | 5/1994 | Tennican et al. | |
| 5,346,475 A | 9/1994 | Gregorio | |
| 5,378,233 A | 1/1995 | Haber et al. | |
| 5,531,691 A | 7/1996 | Shonfeld et al. | |
| 5,562,623 A | 10/1996 | Shonfeld et al. | |
| 5,582,595 A | 12/1996 | Haber et al. | |
| 5,582,598 A | 12/1996 | Chanoch | |
| 5,584,817 A | 12/1996 | van den Haak | |
| 5,688,251 A * | 11/1997 | Chanoch ............ | A61M 5/3146 222/309 |
| 5,819,983 A | 10/1998 | White et al. | |
| 5,971,227 A | 10/1999 | White et al. | |
| 6,004,297 A * | 12/1999 | Steenfeldt-Jensen ........ | A61M 5/31551 604/207 |
| 6,231,550 B1 | 5/2001 | Laughlin | |
| 6,283,941 B1 | 9/2001 | Schoenfeld et al. | |
| 6,533,756 B2 | 3/2003 | Schoenfeld et al. | |
| 6,719,735 B1 | 4/2004 | Gammon | |
| 6,957,752 B2 | 10/2005 | Py et al. | |
| 7,290,573 B2 | 11/2007 | Py et al. | |
| 7,500,959 B2 | 3/2009 | Munk | |
| 7,611,495 B1 | 11/2009 | Gianturco | |
| 7,798,185 B2 | 9/2010 | Py et al. | |
| 7,857,791 B2 | 12/2010 | Jacobs et al. | |
| 7,867,202 B2 | 1/2011 | Moser et al. | |
| 7,959,609 B2 | 6/2011 | Gaydos et al. | |
| 7,967,772 B2 | 6/2011 | McKenzie et al. | |
| 8,057,427 B2 | 11/2011 | Griffiths et al. | |
| 2003/0004467 A1 | 1/2003 | Musick et al. | |
| 2005/0215958 A1 | 9/2005 | Hawthorne | |
| 2007/0016142 A1 | 1/2007 | Burren et al. | |
| 2008/0183138 A1 | 7/2008 | Moser et al. | |
| 2008/0208119 A1 | 8/2008 | Walton et al. | |
| 2009/0221962 A1 | 9/2009 | Kaal et al. | |
| 2009/0275914 A1 | 11/2009 | Harms et al. | |
| 2010/0305512 A1 | 12/2010 | Guillermo et al. | |
| 2010/0331808 A1 | 12/2010 | Py et al. | |
| 2012/0197211 A1 | 8/2012 | Brister | |
| 2013/0150803 A1 | 6/2013 | Shetty et al. | |

FOREIGN PATENT DOCUMENTS

| | | |
|---|---|---|
| DE | 10235468 A1 | 4/2003 |
| EP | 0295075 A1 | 12/1988 |
| EP | 0862731 A1 | 9/1998 |
| EP | 0937471 A2 | 8/1999 |
| EP | 2162230 B1 | 11/2010 |
| FR | 2583291 A1 | 12/1986 |
| GB | 2140302 A | 11/1984 |
| JP | 2000-296178 A | 10/2000 |
| WO | WO 97/19327 A1 | 5/1997 |
| WO | WO 99/38554 A1 | 8/1999 |
| WO | WO 2006/108243 A2 | 10/2006 |
| WO | 2006/114396 A1 | 11/2006 |
| WO | WO 2006/119570 A1 | 11/2006 |
| WO | WO 2006/125329 A1 | 11/2006 |
| WO | WO 2009/003234 A1 | 1/2009 |
| WO | WO 2010/063687 A1 | 6/2010 |
| WO | WO 2011/075760 A1 | 6/2011 |
| WO | WO 2011/137488 A1 | 11/2011 |

OTHER PUBLICATIONS

European Patent Office, Written Opinion in International Patent Application No. PCT/US2012/068210, dated Apr. 24, 2013, 8 pp.
Notification of Transmittal of the International Search Report and Written Opinion of the International Searching Authority, or the Declaration issued in International Application No. PCT/US2016/033950, entitled "Accurate Dose Control Mechanisms and Drug Delivery Syringes," dated Jun. 16, 2017 (17 pages).

* cited by examiner

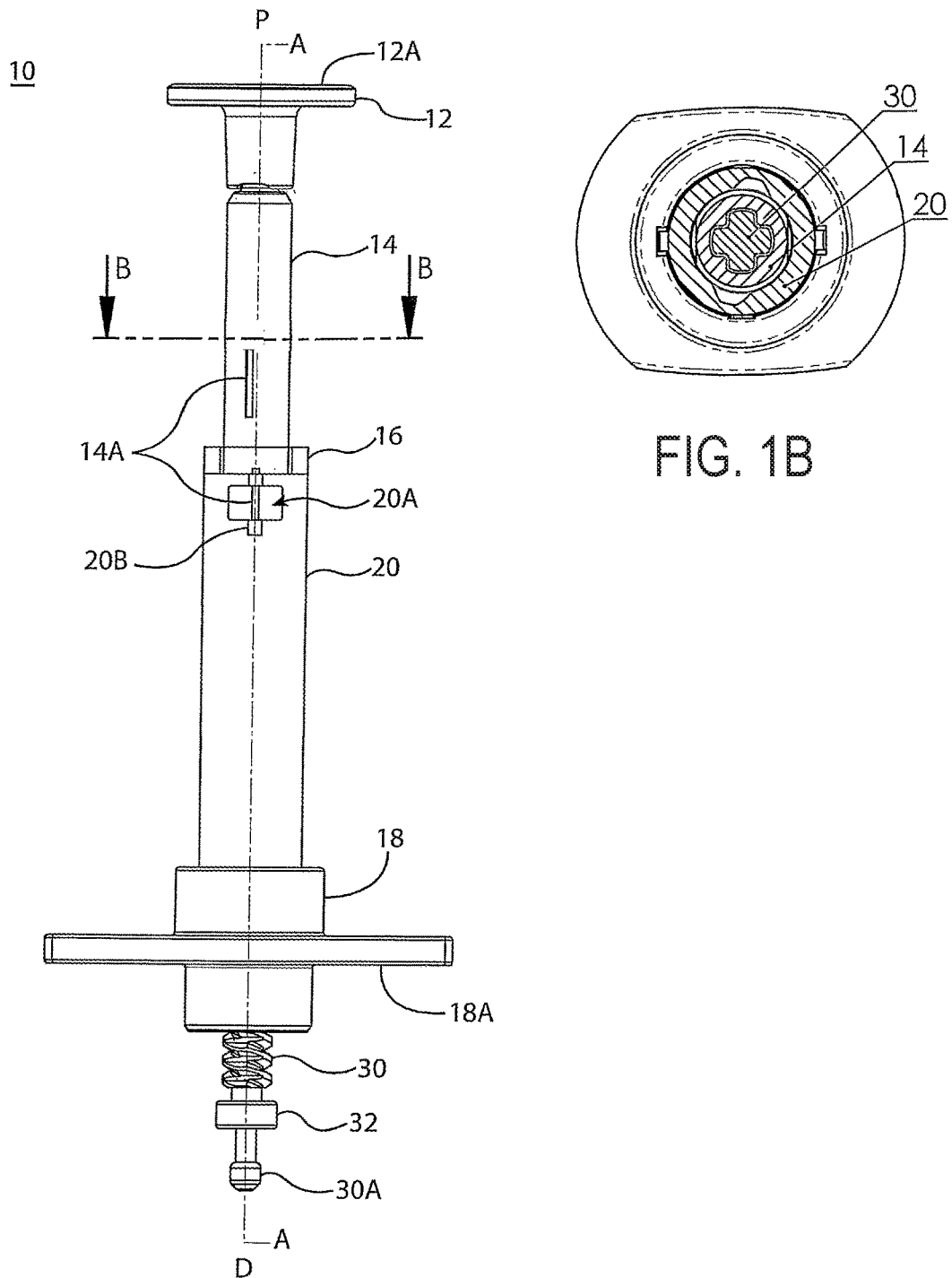

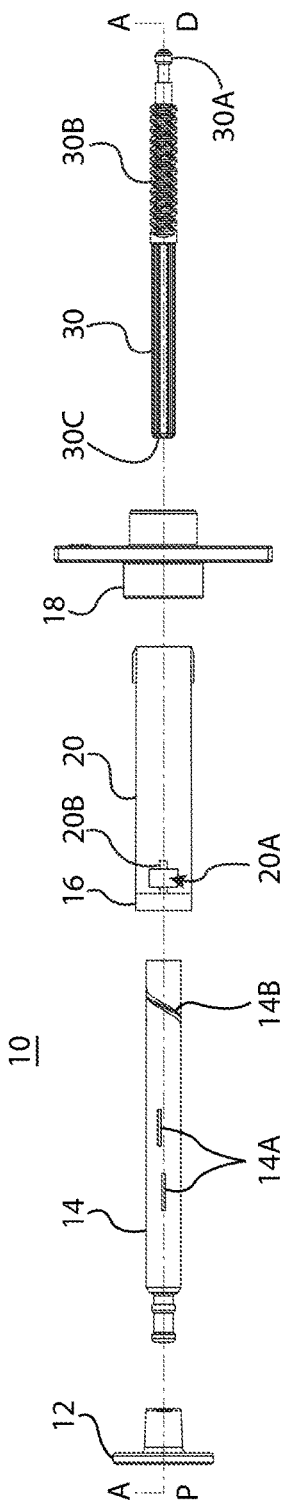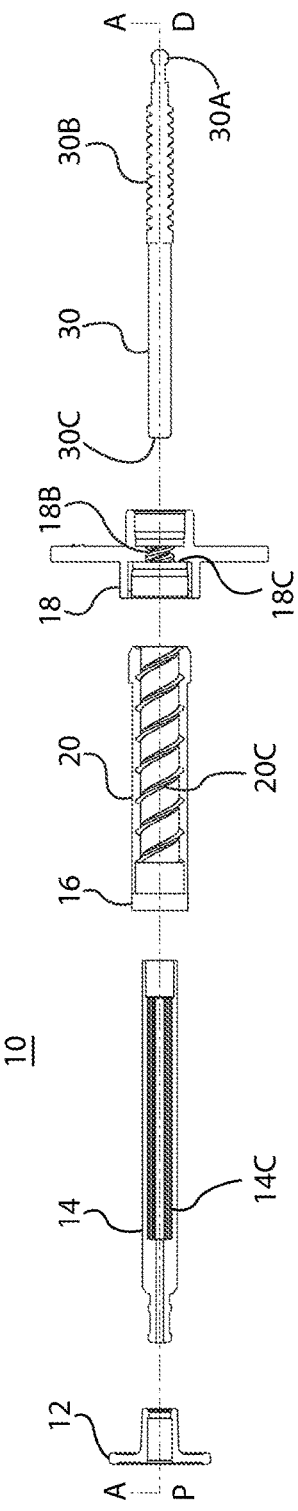
FIG. 3A
FIG. 3B

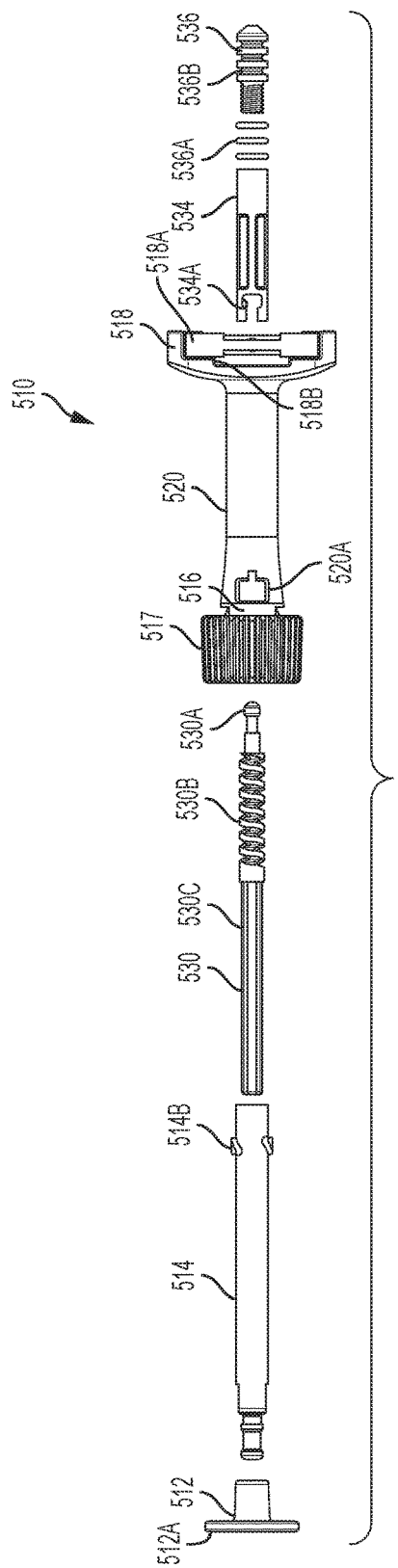
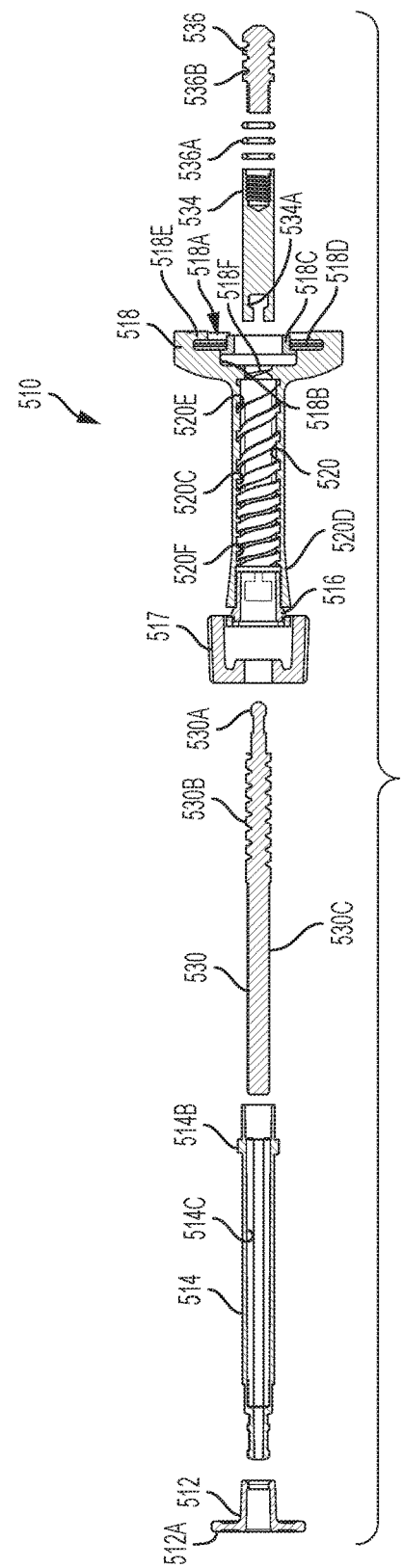

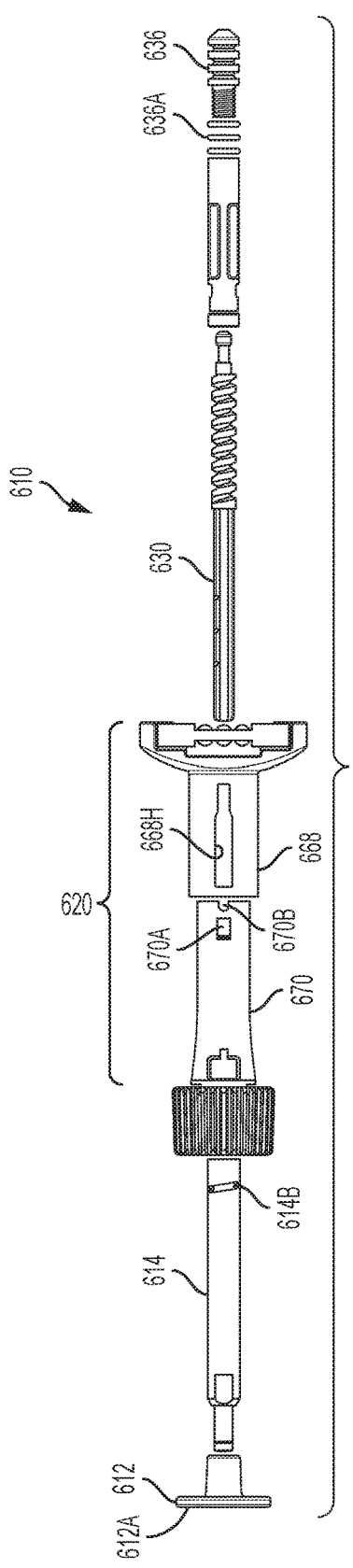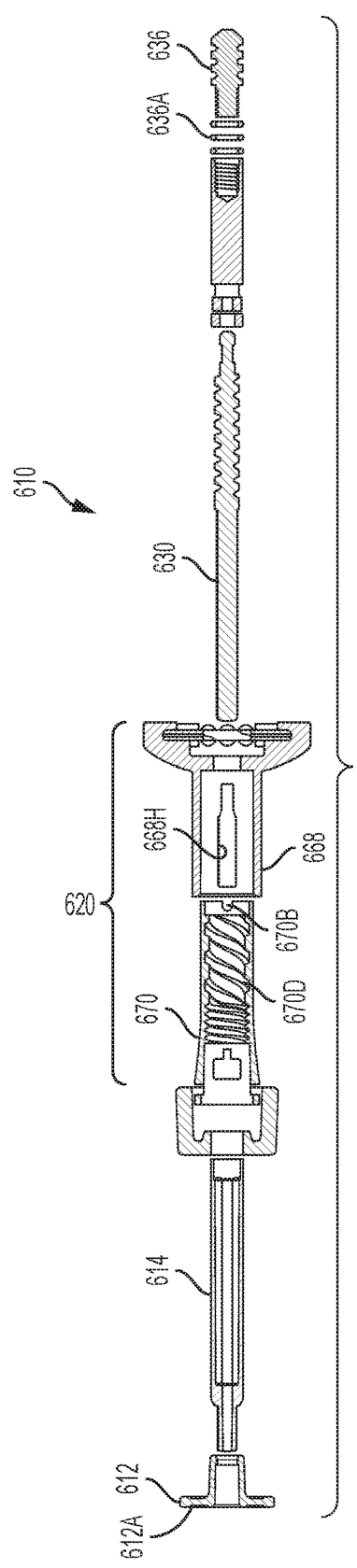

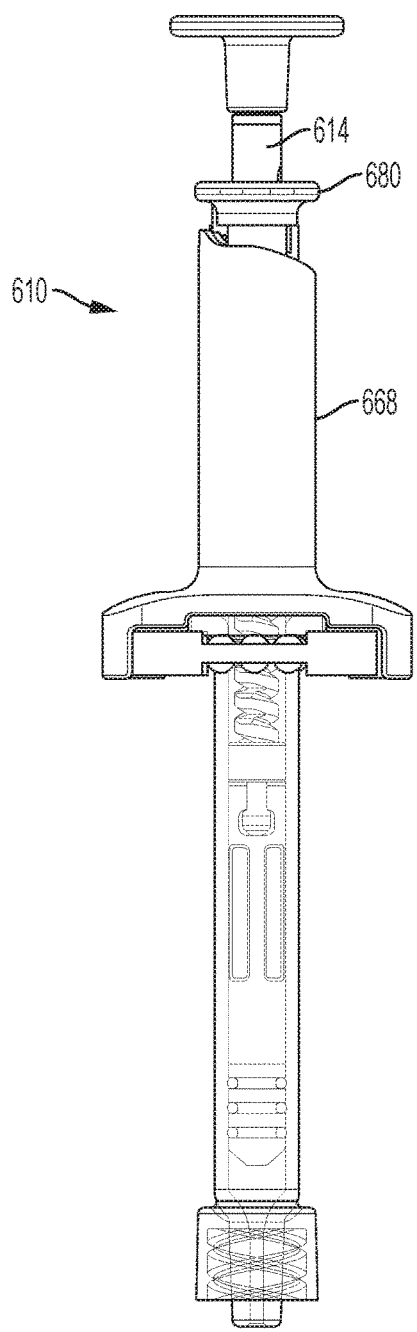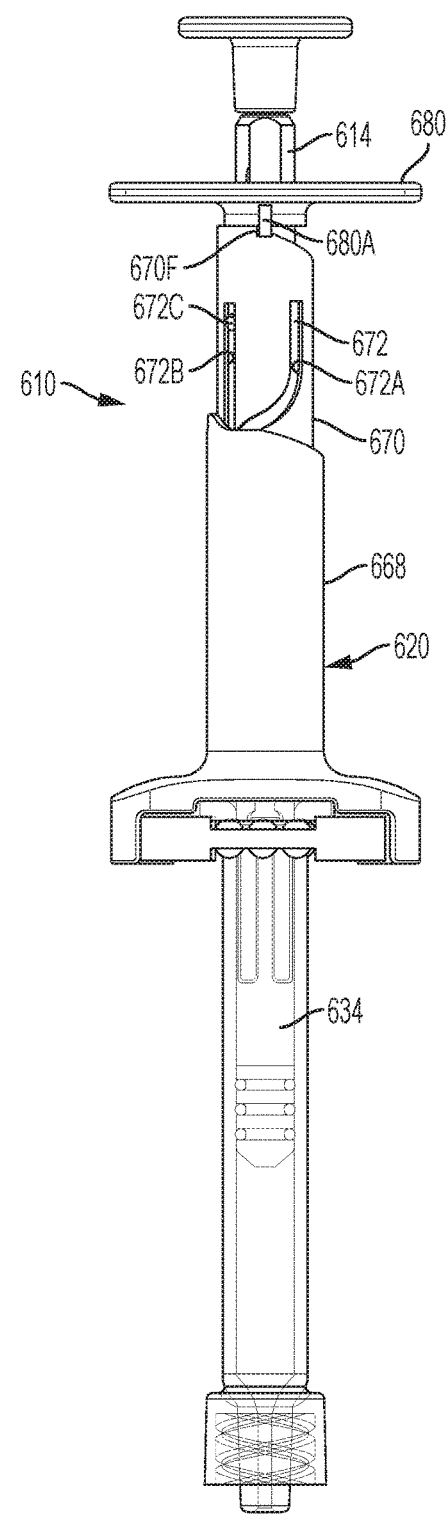
FIG. 12A
FIG. 12B

ACCURATE DOSE CONTROL MECHANISMS AND DRUG DELIVERY SYRINGES

CROSS-REFERENCE TO RELATED APPLICATIONS

This application is a continuation-in-part of U.S. patent application Ser. No. 13/707,201, filed Dec. 6, 2012, which claims priority to U.S. Provisional Patent Application No. 61/568,509, filed on Dec. 8, 2011, both of which are included by reference herein in their entireties for all purposes.

FIELD

THIS INVENTION relates to accurate dose drug delivery syringes. More particularly, this invention relates to accurate dose control mechanisms, drug delivery syringes which incorporate such control mechanisms, the methods of operating such devices, and the methods of assembling such devices.

BACKGROUND

Various studies have shown that the accuracy of dose delivery is affected by a number of factors, including: injection methodologies employed by medical practitioners, an inability to accurately read and control plunger travel during dosing, and the loss of dosage associated with the prime step used to evacuate air from the syringe prior to the dosing step. These effects are particularly magnified by the use of drug delivery syringes that have a high dose volume to axial translation ratio (i.e., a significant quantity of drug is dispensed for even incrementally small distances of plunger depression, as may be the case for large diameter syringes); this problem is more acute when delivering microliter size doses. While these causes for error are common, the need for accurate dose syringes remains. Such syringes are of particular importance in sensitive operations, such as in intravitreal injections, and are very desirable for low dose treatments where inaccurate dosing can lead to substantial error and potential patient harm.

Studies have shown that the amount of treatment delivered may vary significantly depending on whether the medical practitioner chooses to deliver 5 µL (5 microliters) of the treatment by depressing the syringe plunger from 10 µL to 5 µL or by depressing the syringe from 5 µL to 0 µL. Additionally, due to the uncertainty of plunger travel limits some practitioners may depress the syringe past the natural travel limit and deliver excess treatment to the patient because of mechanical compliance between the stopper and the syringe barrel. For example, given a particular syringe barrel diameter, a practitioner may depress the plunger past the natural stop for 0 µL and erroneously deliver up to 20% more dosage than necessary. This error is magnified because of the small dose volume requirements for particular treatments. Because the dosage amount and associated plunger travel distance are small, it is very difficult for a practitioner to gauge the fill amount of the dosing chamber and to control the injection amount as the treatment is applied to the patient. This inaccuracy in dosing can lead to substantial safety risks including, among other side effects, increased pressure in the target region and altered (reduced) drug efficacy.

A primary cause of the dosing inaccuracy is the inability to reliably set the limits of plunger travel, and the inherent variability in the degree to which the plunger seal (or stopper) is depressed at end of delivery during dosing. Also contributing to inaccuracy is the potential variability, during syringe manufacturing, in the placement of reference markings on the syringe barrel. Endemic to these causes of inaccuracy is the high sensitivity of volume dispensed to the axial travel of the plunger, as described above. Mechanical travel limits, however, are difficult to employ in such applications because of the challenges associated with reading and controlling the plunger travel by the user over the small distance of dosing. Simply put, because the dosage amounts are so small, it is difficult for a practitioner to identify the dosage measurements on the syringe barrel and accurately control the plunger depression and dosage amount during injection.

In addition to improving dosing accuracy, it is useful to incorporate the functionality of a priming step into a syringe design to reduce or eliminate air bubbles within the dosing chamber. This step is very useful to minimize safety risks, improve operational hygiene, and reduce pressure in the target site. Minimizing the likelihood of air bubbles during filling helps streamline the drug delivery process for the clinician. Employing pre-filled syringes may assist in the minimization of air bubbles. However, even pre-filled syringes are not fully devoid of air captured during the filling process.

Accordingly, there is a substantial need for syringes which allow the user to readily identify and control the dosage amount, minimize the presence of air bubbles within the dosage chamber prior to drug delivery, and ensure accurate delivery of the required drug dose. It is preferred that such a syringe would enable pre-filling to take advantage of benefits associated with the use of such products.

Further, some medications require mixing two fluids or reconstitution of dry or lyophilized drug prior to an accurate dose injection. This allows, for example, a diluent to be added to a dehydrated, lyophilized, desiccated or powdered active substance immediately prior to injection, which is particularly useful for substances that are subject to degradation or loss of activity when stored in a hydrated form. This also allows for mixing of two liquids, which are mixed just before an injection.

While it is known to provide syringes that comprise a mixing device for mixing deliverable substances prior to injection, the market has been unable to provide such mixing syringes that are capable of providing accurate dosage delivery required for some medications and as discussed above. Examples of such mixing syringes are disclosed, for example, in U.S. patent application Ser. No. 13/566,079, which is assigned to the assignee of this disclosure and incorporated by reference. In addition to the complexities of the structures themselves, the designs may require complex assemblies, multiple operation steps by the user, or other particular nuances that make them difficult to manufacture, assemble, or operate. Further, some mixing syringes must also address factors such as maintenance of container sterility, interaction of components for sealing, venting requirements, and distribution of internal forces, among others. Each of these challenges is further complicated when extreme dose accuracy is required.

SUMMARY

The present invention provides dose control mechanisms, which allow for the accurate dosing and delivery of drug treatments, and drug delivery syringes which incorporate such control mechanisms. Such novel devices permit the identification and control of the dosage amount, permit the syringe to be "primed" (i.e., evacuated of air bubbles) prior to drug delivery, and ensure the accurate delivery of microliter volume dosages, all within a device size that is similar to commonly used conventional syringes available in the marketplace. Such novel devices are safe and easy to use, and are aesthetically and ergonomically appealing for clinical practitioners without significantly altering technique currently employed by clinicians to administer injectable medications. The novel devices of the present invention provide these desirable features without any of the problems associated with known prior art devices.

In a first embodiment, the present invention provides a dose control mechanism for a syringe. The control mechanism includes a plunger having a coarse pitch screw on its exterior surface, a housing having a corresponding coarse pitch guide along the interior surface of the housing, a screw having a fine pitch screw which interfaces with a fine pitch nut of an adapter, wherein the plunger has an internal annular space within which screw at least partially resides. The plunger having the coarse pitch is rotatable upon the corresponding coarse pitch guide, and wherein at least a portion of the plunger is rotationally keyed to interface with a corresponding rotationally keyed portion of the screw. A pitch ratio between the coarse pitch screw and the fine pitch screw is from approximately 1:1 to approximately 20:1, more specifically from approximately 2:1 to approximately 10:1, and more preferably from approximately 4:1 to approximately 8:1. In a preferred embodiment, the pitch ratio of the coarse pitch screw 14B and the fine pitch screw 30B is approximately 4:1. The screw may further include a screw connection aspect and, optionally, a ring which function to connect the screw to the plunger seal directly or to a plunger rod. In at least one embodiment, the housing has a housing cover at its proximal end and a window to permit the user to view the location of the plunger within the housing. The plunger may have one or more dose markings on the external surface of the plunger and the housing may have one or more guide markings with which to align plunger dose markings. Upon use by the user, the plunger axially translates a first distance D1 causing the screw to axially translate a second distance D2, wherein D1 is always greater than D2 by a factor determined by the pitch ratio.

In a second embodiment, the present invention provides an accurate dose drug delivery syringe having a dose control mechanism, a barrel, a plunger seal, and a barrel adapter assembly having a barrel tip and a needle. The syringe may further include a plunger rod connected at one end to the screw and at another end to the plunger seal. The syringe may be a fill-at-time-of-use syringe, a pre-filled syringe, or a safety syringe, or a combination thereof. The housing of the syringe may have a housing cover at its proximal end to protect the interior of the housing from the environment and a window to permit the user to view the location of the plunger within the housing. The plunger may have one or more dose markings on the external surface of the plunger, and the housing may have one or more guide markings at the window with which to align plunger dose markings. Upon use by the user, the plunger axially translates a first distance D3 causing the screw to axially translate a second distance D4.

The dose control mechanism may also be designed to provide a desired axial movement of the screw relative to the axial movement of the plunger. In other words, the dose control mechanism may be tailored to provide a desired feel to the user by way of the plunger, while providing a desired axial movement of the screw and associated administration of medication. In an embodiment, the plunger and housing are coupled together by way of a variable pitch screw. The pitch may be varied over the length of the travel of the plunger relative to the housing, or the travel may include two or more distinct or transitional pitches. In any case, however, the variable pitch will provide at least two pitches.

In an embodiment, for example, the housing includes at least one variable pitch thread along its inner diameter, and the plunger includes at least one thread segment disposed to engage the variable pitch thread of the housing. According to a preferred embodiment, the variable pitch thread of the housing includes a fine pitch thread toward its proximal end and a coarse pitch thread towards it distal end. Thus, if the user applies a substantially constant speed movement of the plunger as it is depressed, as the thread segment of the plunger moves along the fine pitch, the plunger and the keyed screw will rotate at a first speed, while the plunger and keyed screw will rotate at slower speed as the thread segments of the plunger engage the coarse thread disposed toward the distal end of the housing. In this way, the rotations of the plunger, and associated screw, may be tailored to a wide range of rotational speeds, and, therefore, axial movements of the screw by utilizing a variable pitch screw engagement between the plunger and the housing.

The fine portion of the variable pitch thread may have a 1:1 pitch ratio with the thread of the adapter while the coarse portion of the variable pitch thread may have a ratio of up to approximately 20:1 with the thread of the adapter as described above.

The variable pitch thread may provide numerous advantages. For example, the syringe may be configured to be filled at time of use. The variable pitch may allow the syringe to be filled more quickly.

The housing may be provided in one or more components. By way of example only, the housing may include two or more housing sections that include threads of respective pitches, potentially providing advantages regarding the fabrication process. By way of further example, the housing may include a lower housing section having a coarse pitch and an upper housing section having a fine pitch. The components of the housing may be assembled by any appropriate coupling arrangement, including, but not limited to, spin welding, adhesive, or coupling structure, such as threads or engaging latches or the like.

In another embodiment, the dose control mechanism further includes a housing including first and second housing sections that are moveable relative to one another. For example, a second housing section may be positioned between the first housing section and the plunger. In such an embodiment, the second housing section includes an internal thread—which can be either constant pitch or variable pitch—configured to engage the external thread segments of the plunger. The second housing section is configured such that, in a first configuration, it is able to axially translate with respect to the first housing section. In a second configuration, the second housing section is fixed in relation to the first housing section. As will be explained below, this allows a syringe to be quickly filled and primed in a way that is familiar to the user, while providing accurate dose control during delivery.

According to one aspect of the invention, there is provided a dose control mechanism for a syringe, and a syringe including such a dose control mechanism. One embodiment of such a dose control mechanism includes a housing, an adapter, a plunger, and a screw. The housing includes a longitudinally extending channel having an interior surface. The adapter includes a channel having a fine pitch thread. The plunger has an exterior surface and an axially extending channel; the axially extending channel includes a first key aspect. The screw includes a screw exterior surface that includes a second key aspect along a proximal portion of the screw exterior surface. A proximal end of the screw is disposed at least partially within the axially extending channel of the plunger. At least a portion of the second key aspect is disposed within the axially extending channel of the plunger and engaging the first key aspect for sliding movement such that rotational movement of the plunger causes rotational movement of the screw. A distal portion of the screw exterior surface includes a fine pitch screw thread at least partially disposed within and interfacing with the fine pitch thread of the adapter. An engaging screw thread arrangement is provided between the plunger and the housing. The engaging screw thread arrangement includes at least one thread segment and a pitch guide including a variable pitch thread. At least a portion of the longitudinally extending channel of the housing includes one of the pitch guide and the at least one thread segment, and the plunger includes the other of the pitch guide and the at least one thread segment. The plunger resides at least partially within the housing with the at least one thread segment engaged with the pitch guide. In at least one embodiment of the dose control mechanism, the variable pitch thread includes at least two different thread pitches. In at least an additional embodiment, the variable thread pitch continually varies along at least a portion of the variable thread pitch.

At least an additional embodiment of such a dose control mechanism includes a housing, an adapter, a plunger, and a screw wherein the housing has a longitudinally extending channel having an interior surface, and includes at least a first housing section and a second housing section disposed for telescoping movement relative to one another between a retracted position and an extended position. The adapter includes a channel having a fine pitch thread. The plunger has an exterior surface and an axially extending channel, the axially extending channel including a first key aspect. A proximal end of the screw is disposed at least partially within the axially extending channel of the plunger. The screw has a screw exterior surface including a second key aspect along a proximal portion. At least a portion of the second key aspect is disposed within the axially extending channel of the plunger and engaging the first key aspect for sliding movement such that rotational movement of the plunger causes rotational movement of the screw. a distal portion of the screw exterior surface includes a fine pitch screw thread at least partially disposed within and interfacing with the fine pitch thread of the adapter. An engaging screw thread arrangement is provided between the exterior surface of the plunger and the housing. The engaging screw thread arrangement includes at least one thread segment and a pitch guide including a thread. At least a portion of the longitudinally extending channel of the housing includes one of the pitch guide and the at least one thread segment; the plunger includes the other of the pitch guide and the at least one thread segment. The plunger resides at least partially within the housing with the at least one thread segment engaged with the pitch guide. According to at least one embodiment, the first housing section and the second housing section are disposed for movement between a retracted position and a primed position. According to at least one embodiment, rotational movement is permitted between the first and second housing sections as they telescope relative to one another between the retracted and extended positions.

Additionally, in at least one embodiment, the dose control mechanism includes a dose feedback mechanism. The feedback mechanism may provide tactile feedback to the user for, for example, identification of the desired delivery volume. When the user dials the plunger rod/screw to their desired dose volume (i.e., when they the desired microliter setting in the window), they will feel a tactile notch or stop-point so they know that they should check to see if they have reached the desired dose volume. The feedback mechanism may include multiple volume-based detents to indicate, for example, when the syringe is at the 20 microliter, 10 microliter, and 5 microliter delivery volumes. In one embodiment, one or more clips can be attached to the housing to engage with the plunger rod/screw at axial locations which correspond with one or more desired set-points/stop-points. The clip may have one or more radially inward extending prongs which pass-through corresponding apertures in the housing at, for example, the screw-threaded portion of the housing. The clip prongs are configured to removably engage or contact one or more corresponding recesses, divots, apertures or the like in the plunger rod/screw. As the user axially rotates the plunger rod/screw to dial their desired delivery volume, the clip prongs are caused to contact/engage the screw recess which corresponds to a defined set-point/stop-point. The set-points/stop-points recesses are dimensioned such that each corresponds with the amount of drug volume in the syringe for drug delivery. Accordingly, multiple clips containing clip prongs can be used to engage the housing through multiple apertures in order to engage the plunger rod/screw at various set-point recesses along the axial length of the plunger rod/screw to give one or more tactile feedbacks to the user regarding the dialed dose volume within the syringe. In another embodiment, the clip prongs may be pre-established and molded as radially inward aspects on the housing.

In a further embodiment, a method of manufacturing a syringe having a control mechanism includes the steps of: (i) mounting a barrel adapter assembly to a distal end of a syringe barrel; (ii) mounting a plunger seal through a proximal end of the syringe barrel; and (iii) mounting a control mechanism to the proximal end of the syringe barrel, wherein the control mechanism may rest in contact with the plunger seal. The method may further include, before the step of (ii) mounting a plunger seal through a proximal end of the syringe barrel, the step of: filling the barrel at least partially with a fluid substance. In at least one embodiment, the adapter is a two component adapter having a proximal adapter portion and a distal adapter portion. The proximal adapter portion has one or more connection prongs and the distal adapter portion has corresponding connection ports which, when forced together, connection prongs and corresponding connection ports merge, mate, or otherwise connect to unite the two portions of the adapter. Steps (i) and (ii), and the optional step of filling the barrel at least partially with a fluid substance, may be performed in a sterile environment to maintain the container integrity and sterility of the syringe.

The present invention further provides methods of assembling dose control mechanisms, methods of manufacturing syringes having dose control mechanisms, and methods of operation of such mechanisms and syringes. Such novel devices and methods permit the identification and control of the dosage amount, permit the syringe to be "primed" (i.e., evacuated of air bubbles) prior to drug delivery, and ensure the accurate delivery of microliter volume dosages, all within a device size that is similar to commonly used conventional syringes available in the marketplace. Throughout this specification, unless otherwise indicated, "comprise," "comprises," and "comprising," or related terms such as "includes" or "consists of," are used inclusively rather than exclusively, so that a stated integer or group of integers may include one or more other non-stated integers or groups of integers. As will be described further below, the embodiments of the present invention may include one or more additional components which may be considered standard components in the industry of medical devices. The components, and the embodiments containing such components, are within the contemplation of the present invention and are to be understood as falling within the breadth and scope of the present invention.

BRIEF DESCRIPTION OF THE DRAWINGS

The following non-limiting embodiments of the invention are described herein with reference to the following drawings, wherein:

FIG. 1A shows a side elevational view of a dose control mechanism, according to at least one embodiment of the present invention;

FIG. 1B shows a cross-sectional view in a plane "B" which is perpendicular to axis "A" of the dose control mechanism of FIG. 1A;

FIG. 3A shows an exploded view, exploded along an axis "A," of the dose control mechanism shown in FIG. 1A;

FIG. 3B shows a cross-sectional exploded view, exploded along an axis "A," of the dose control mechanism shown in FIG. 1A;

FIG. 9A shows an exploded view, exploded along a longitudinal axis of the dose control mechanism shown in FIGS. 8A-8C;

FIG. 9B shows a cross-sectional exploded view, exploded along a longitudinal axis of the dose control mechanism shown in FIGS. 8A-8C;

FIG. 11A is an exploded view of the dose control mechanism of FIGS. 10A-10F, exploded along a longitudinal axis;

FIG. 11B is a cross-sectional exploded view of the dose control mechanism shown in FIGS. 10A-11A, exploded along a longitudinal axis;

FIG. 12A is a side elevational view of another embodiment of a dose control mechanism according to the present invention, the housing being illustrated in a retracted position;

FIG. 12B is a side elevational view of the dose control mechanism of FIG. 12A, the housing being illustrated in an extended position;

DETAILED DESCRIPTION

Figures 2A, 2B:
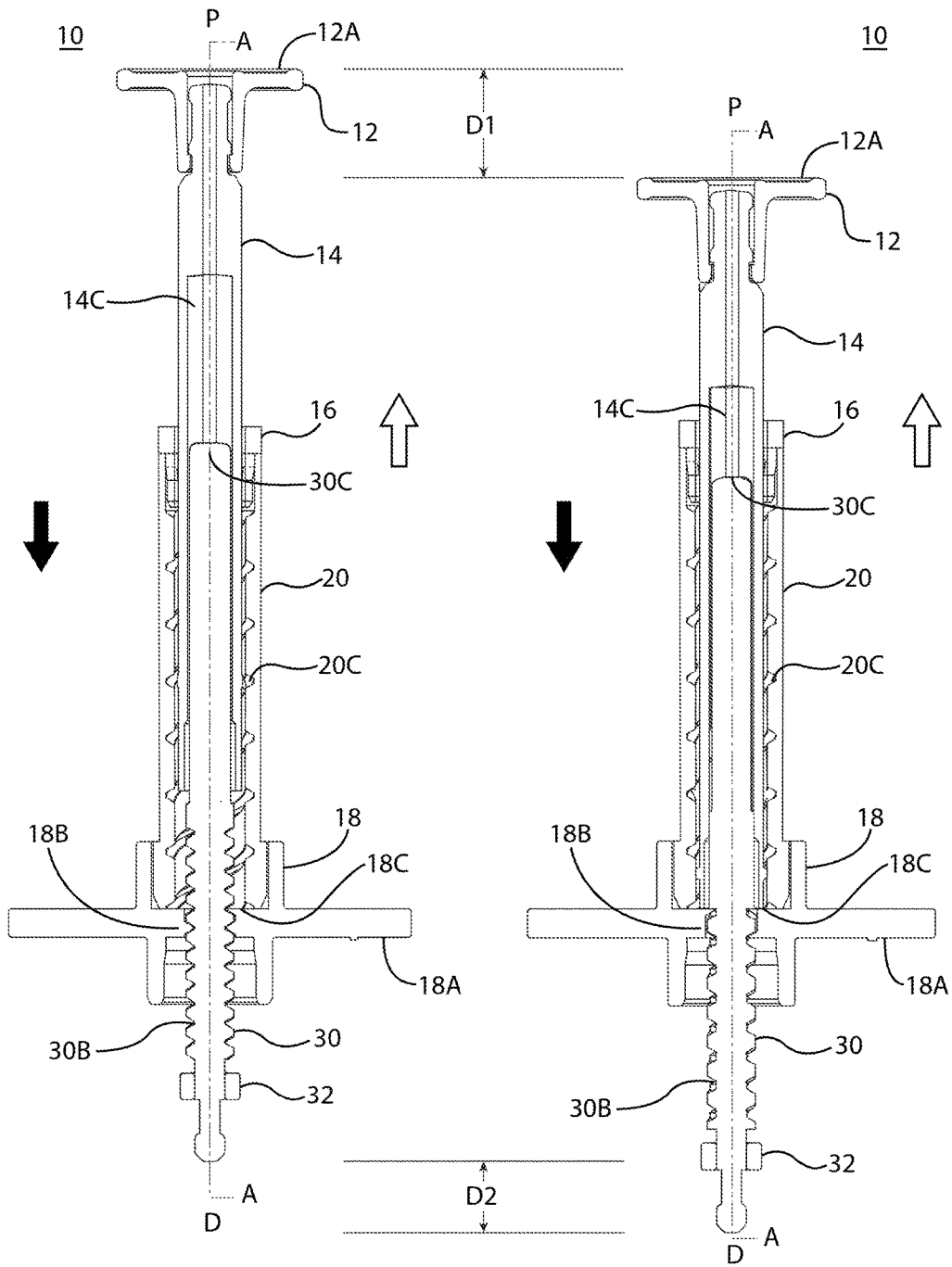
FIG. 2A shows a cross-sectional view of the dose control mechanism shown in FIG. 1A as the components may appear in a ready-to-inject stage of operation.
FIG. 2B shows a cross-sectional view of the dose control mechanism shown in FIG. 1A as the components may appear in an end-of-dose stage of operation.

As used herein to describe the dose control mechanisms, drug delivery syringes, or any of the relative positions of the components of the present invention, the terms "axial" or "axially" refer generally to a longitudinal axis "A" around which the control mechanisms and syringes are preferably positioned, although not necessarily symmetrically therearound. The term "radial" refers generally to a direction normal to axis "A". The terms "proximal," "rear," "rearward," "back," or "backward" refer generally to an axial direction in the direction "P". The terms "distal," "front," "frontward," "depressed," or "forward" refer generally to an axial direction in the direction "D". As used herein, the term "glass" should be understood to include other similarly non-reactive materials suitable for use in a pharmaceutical grade application that would normally require glass, including but not limited to certain non-reactive polymers such as cyclic olefin copolymers (COC), cyclic olefin polymers (COP), and the like. The term "plastic" may include both thermoplastic and thermosetting polymers. Thermoplastic polymers can be re-softened to their original condition by heat; thermosetting polymers cannot. As used herein, the term "plastic" refers primarily to moldable thermoplastic polymers such as, for example, polyethylene and polypropylene, or an acrylic resin, that also typically contain other ingredients such as curatives, fillers, reinforcing agents, colorants, and/or plasticizers, etc., and that can be formed or molded under heat and pressure. As used herein, the term "plastic" is not meant to include glass, non-reactive polymers, or elastomers that are approved for use in applications where they are in direct contact with therapeutic liquids that can interact with plastic or that can be degraded by substituents that could otherwise enter the liquid from plastic. The term "elastomer," "elastomeric" or "elastomeric material" refers primarily to cross-linked thermosetting rubbery polymers that are more easily deformable than plastics but that are approved for use with pharmaceutical grade fluids and are not readily susceptible to leaching or gas migration under ambient temperature and pressure. "Fluid" refers primarily to liquids, but can also include suspensions of solids dispersed in liquids, and gasses dissolved in or otherwise present together within liquids inside the fluid-containing portions of syringes. According to various aspects and embodiments described herein, reference is made to a "biasing member", such as in the context of one or more biasing members for retraction of a needle or needle assembly. It will be appreciated that the biasing member may be any member that is capable of storing and releasing energy. Non-limiting examples include a spring, such as for example a coiled spring, a compression or extension spring, a torsional spring, and a leaf spring, a resiliently compressible or elastic band, or any other member with similar functions. In at least one embodiment of the present invention, the biasing member is a spring, preferably a compression spring.

The novel devices of the present invention provide dose control mechanism, which allow for the accurate dosing and delivery of drug treatments, and drug delivery syringes which incorporate such control mechanisms. Such devices are safe and easy to use, and are aesthetically and ergonomically appealing for clinical practitioners. The devices described herein incorporate features which make activation, operation, and lock-out of the device simple for even untrained users. The novel devices of the present invention provide these desirable features without any of the problems associated with known prior art devices. Certain non-limiting embodiments of the novel dose control mechanisms, drug delivery syringes, and their respective components are described further herein with reference to the accompanying figures.

Various studies have shown that the accuracy of dose delivery using conventional syringes is affected by a number of factors, including an inability to accurately read and control plunger travel during dosing. The use of conventional drug delivery syringes that have a high dose volume to axial translation ratio (i.e., a significant quantity of drug is dispensed for even incrementally small distances of plunger depression, as may be the case for large diameter syringes) significantly magnifies this inaccuracy. With the growth of high-cost, low-volume drug treatments entering the marketplace, it is increasingly important to accurately dose and deliver such low-volume treatments to the patient. The embodiments of the present invention overcome the challenges faced with the use of conventional syringes for the dosing and delivery of low-volume treatments by utilizing novel dose control mechanisms. As will be described further herein, the novel dose control mechanisms permit the user to accurately read and dose the desired volume of drug treatment for delivery to the patient. These devices permit the user to have a normal range of thumb travel, as they may otherwise expect with a conventional syringe, but transform that range of thumb travel to a very finite (e.g., smaller or incremental) range of plunger seal travel. This relationship allows the user to utilize the syringe without additional training, but with the significant benefit of incremental, low-volume dose control.

FIG. 1A shows an embodiment of a novel dose control mechanism for a syringe, according to at least one embodiment of the present invention. The control mechanism 10 includes a plunger 14, a housing 20, an adapter 18, and a screw 30. The plunger 14 may include a button 12 as a unified or separate component. For example, button 12 may be a preformed aspect at the proximal end of the plunger 14. Alternatively, button 12 may be a separate component attached to the proximal end of plunger 14 by a snap-fit. In a preferred embodiment, the button 12 may be attached to plunger 14 but allowed to axially rotate freely from plunger 14, but rotationally fixed relative to the user's/clinician's finger. Regardless of the specific configuration and relationship of button 12 and plunger 14, button 12 is intended to have a user interface surface 12A for contact and control by a user (e.g., such as with the thumb or finger tip of the user).

Housing 20 has a substantially cylindrical axial passthrough within which a substantially cylindrical plunger 14 may at least partially reside. The distal end of the housing 20 is connected to, and/or resides partially within, a proximal portion of adapter 18. The proximal and distal portions of adapter 18 may be separated by an adapter flange 18A which may additionally serve as a finger flange for use by the user. The internal aspects of these components will be described in further detail herein with reference to FIGS. 1B, 2A, 2B, and 3B. Screw 32 may reside at least partially within housing 20 and plunger 14, and extends distally beyond flange 18. Screw 30 may have a screw connection 30A aspect and, optionally, a ring 32, to facilitate integration of the control mechanism with a drug delivery syringe and to center the plunger rod.

Housing 20 may optionally include housing cover 16 at its proximal end, for example, to close the interior of the housing 20 off from the environment and/or to axially align plunger 14 within housing 20, and to prevent removal of the plunger rod by functioning as a mechanical stop. Housing 20 may further include a window 20A, which may be an opening (e.g., an aperture) in the housing or a transmissive or translucent component. Regardless of the particular configuration of window 20A, its primary purpose is to permit the user to view the location of the plunger 14 within housing 20. Plunger 14 may include one or more dose markings 14A on the external surface of the plunger 14. Housing 20 may have one or more reference or guide markings 20B, such as at the window 20A, with which to align plunger dose markings 14A. The plunger dose markings 14A may correspond to the relevant dose amounts desired by the user. By employing the respective plunger and housing markings, the user can control the volumetric dose quantities desired for delivery to the patient, as will be explained further herein. In another embodiment, the window 20A may be covered by a lens, such as a clear lens, that provides visual magnification.

FIGS. 2A and 2B show cross-sectional views of the dose control mechanism, according to at least one embodiment of the present invention, in a ready-to-inject stage and in an end-of-dose stage, respectively. The cross-sectional views show certain other aspects of the components which are internal to the mechanism. As shown, plunger 14 has an internal annular space 14C within which screw 30 at least partially resides. Plunger 14 has a coarse pitch male thread 14B (visible in FIG. 3A) on its exterior surface which interfaces with the coarse pitch guide 20C along the interior surface of the housing 20 such that, in at least one embodiment, the pitch on guide 20C is the same as pitch on plunger thread 14B. Similarly, screw 30 has a fine pitch thread 30B which interfaces with a fine pitch nut 18B of adapter 18 such that, in at least one embodiment, the pitch on screw thread 30B is the same as pitch on nut 18B. Also visible in FIGS. 2A and 2B are the proximal end 30C of screw 30 and ledge 18C of adapter 18. The plunger 14 having the coarse pitch 14B is rotatable upon the corresponding (e.g., "female") coarse pitch guide 20C, which is rotationally keyed to the screw 30 having the fine pitch thread 30B. The terms "male" and "female" are intended to describe corresponding and interfacing threads or surfaces, and can be used interchangeably to describe corresponding aspects as would be readily appreciated in the art. The screw 30 having the fine pitch screw 30B engages the female fine pitch nut 18B of the adapter 18. Hence, rotation of plunger 14 results in axial translation of screw 30 and the resolution of axial travel is dictated by pitch 30B.

Because the plunger 14 and screw 30 are rotationally keyed, each having a respective screw pitch, rotational translation of the plunger 14 rotates and axially translates the screw 30. The term "keyed" is used herein to mean any number of internal aspects which removably or slidably (in the axial sense) connect two or more components. For example, the plunger 14 may be a hollow cylinder having a coarse pitch screw on at least some portion of the outer surface and a spline design along at least a portion of the inner surface. The spline design is configured to mate with, and transform or relay rotation to, a complimentary spline contained at a proximal end of the screw 30. This spline design element ensures that the plunger 14 and screw 30 are rotationally keyed. The spline or rotationally keyed aspect is visible at the proximal end 30C of screw 30 in FIG. 3A, and with its corresponding spline or rotationally keyed aspect in the annular space 14C of plunger 14 in FIG. 3B. Any number of corresponding shapes may be utilized to impart a rotationally "keyed" relationship between these components such that the first component may removably or slidably engage the second component in a manner which enables the rotational keyed relationship and permits axial slip. Such components may alternatively be keyed to have the shape of, for example, a cross or plus, a horizontal line or minus, a star, or a semi-circle shape, with the corresponding component having the inverse of the shape on an interior annular space. FIG. 1B shows a cross-sectional view in a plane "B" which is perpendicular to axis "A" of the dose control mechanism of FIG. 1A. As shown in FIG. 1B, in at least one embodiment, screw 30 has a cross or plus shape in its perpendicular cross-section which is keyed to plunger 14. This arrangement or configuration allows the two components to be rotationally keyed while allowing them to axially slip past each other. Both screw 30 and plunger 14 reside, at least partially and/or at some point of operation, within housing 20.

Fine pitch nut 18B (or simply "nut"), having the same fine pitch of the screw 30, may be used to brace the screw 30 and facilitate the transfer of the rotational movement of the plunger 14 into axial translation of the screw 30. The pitch ratio of the coarse pitch to the fine pitch dictates the degree or resolution of axial travel of the screw 30, i.e., the distance that the screw 30 axially translates for each rotation of the plunger 14. As a result, the medical practitioner is provided with an ease of operation that enables them to accurately read and set the dosage amount. The pitch ratio can be set to enable "fine tuning" of the dosage amount, which is of particular importance for low-volume dosage quantities where variance may be significantly affected by plunger travel.

During operation of the dose control mechanism, the user may axially rotate plunger 14 or depress the button 12 to control the desired dosage volume for injection into the patient. Axial rotation of the plunger 14 causes coarse pitch screw 14B (visible in FIG. 3B) to travel within the corresponding coarse pitch guide 20C of housing 20, as shown in FIGS. 3A and 3B. This action causes the plunger 14 to axially translate in the distal direction thereby reducing the dosage volume within the drug chamber, as is explained in more detail herein. Because of the rotationally keyed interaction between plunger 14 and screw 30 within the annular space 14C, rotation of the plunger 14 causes screw 30 to axially rotate and translate. However, because of the pitch ratio between the plunger 14 and screw 30, each unit measure of translation in the distal direction of the plunger 14 results in fractional (e.g., smaller, more resolved) translation of the screw 30 in the distal direction. This has a number of benefits for accurate control during delivery of low-volume doses. Primarily, the pitch ratio relationship permits the user to accurately control the desired dose and delivery of a drug treatment. Additionally, this pitch ratio relationship allows the user to operate a syringe in a conventional manner, such as by depressing the plunger 14 a noticeable distance, while only resulting in fractional or small translation of the screw.

The novel dose control mechanisms of the present invention also utilize features which provide integrated and adjustable range-of-travel limits to ensure accurate delivery of low-volume drug treatments. This may be enabled, for example, by incorporating features that prevent variable depression of the plunger seal (or stopper) (e.g., preventing the plunger from "bottoming out" during drug delivery) within a syringe. Specifically, the dose control mechanisms of the present invention utilize adjustable set mechanical end-points for the range of plunger axial travel during drug delivery. Such limits may be predefined, i.e., integrated and fixed into the syringe configuration in advance of use by the medical practitioner, or adjustable, i.e., variably controlled by a compounding pharmacist, a medical practitioner, or by a self-administering patient using an integrated dosage setting mechanism. Such mechanical set-points permit a range of axial plunger travel that are, for example, related to the priming and dosing quantities, but also prevent the user from variably depressing the plunger and plunger seal as part of the dosing stroke or from bottoming out these components within the dosing chamber of a syringe. This novel control mechanism greatly increases the accuracy of the dose delivered to the patient. Additionally, embodiments of the present invention allow the user to prime the syringe to evacuate the dosing chamber of any residual air prior to delivering the dose to the patient. The prime step may be a fixed amount or a variable amount, depending on the configuration of the low dose syringe and variation in amount of drug or liquid contained/filled in the dosing chamber. The configuration of the novel syringe allows the user to complete the prime step while maintaining, or enabling, the ability of the syringe to deliver an accurate and precise dose to the patient.

As stated above, the mechanical set-point limits effectively function to prevent the user from variably depressing the plunger and plunger seal or from bottoming out these components within the dosing chamber of a syringe. This functionality increases the accuracy of the dose delivered to the patient because it reduces the variability of the delivered dose from the amount prescribed and intended to be delivered to the patient. The mechanical end-points may be readily identified and easily set by employing the pitch ratio between the plunger 14 having a coarse pitch screw 14B and the screw 30 having a fine pitch screw 30B. For example, in one such embodiment a pitch ratio between the coarse pitch and a fine pitch may be 4:1, such that rotationally "screwing" or turning plunger 14 axially translates the plunger component four times as far as the axial translation of the screw component. Accordingly, the practitioner is provided with a significant ease of operation since they may more accurately set the required dosage amount. Such a pitch ratio may be, for example, anywhere from the range of 1:1 to 20:1, as may be necessary to obtain the required accuracy of the low-volume dosage amount. The "dialing-in" or "setting" may be facilitated by the dose markings on the plunger and guide markings on the housing described above.

As the user depresses the button 12, which rotates the plunger 14 to set the desired low-volume dosage for injection, they can perform what is known in the art as a "priming step." This priming step evacuates the dosing chamber of any residual air bubble captured in the dosing chamber during pre-filling, if any, and primes the attached needle (or catheter or an extension set) before delivery. After priming and setting of the dose by depression of the button 12 has been completed, the button 12 may be depressed further to bottom out and, hence, inject the desired dose amount to the patient. Upon drug dose delivery, the plunger 14 is caused to "bottom out" on ledge 18C of adapter 18 (as shown in FIG. 2B). Because of the pitch ratio between the plunger 14 and the screw 30, as plunger 14 is depressed or axially translated in the distal direction (i.e., in the direction of solid arrow in FIGS. 2A and 2B), screw 30 is caused to axially translate in the distal direction only a fraction of the distance translated by the plunger 14. This difference in axial translation distance between plunger 14 and screw 30 is visible by comparing distances D1 and D2 in FIGS. 2A and 2B. D1 is the distance that plunger 14 axially translates while D2 is the incremental distance that screw 30 axially translates. The difference in dimensions D1 and D2 is also clear by the reduction in the annular space 14C of plunger 14 (compare FIGS. 2A and 2B), when identifying the relative position of the proximal end 30C of the screw 30. Accordingly, the variable annular space 14C of plunger 14 is related to the mechanical set-point desired by the practitioner and provides space for translation of the screw 30 during the dosage stroke.

Notably, the novel embodiments contemplated by the present invention effectively prevent the plunger seal from "bottoming-out" within the dosing chamber. This pre-empts one aspect of user variability in either excess dosing by over-depression of the plunger or under dosing by under-depression of the plunger, ensuring that the quantity dosed to the patient is accurate and minimizes user error. This is of particular importance in low dosage treatments, where user-related errors can cause significant and undesirable variation and inaccuracy in the delivery of medication to the patient. The embodiments according to the present invention prevent such occurrences and work to effectively eliminate the dosing errors associated with prior syringe configurations and delivery methodologies. Furthermore, depression of the plunger in this embodiment does not back-drive the screw.

The novel dose control mechanisms of the present invention can be integrated into a number of drug delivery syringe configurations to provide accurate dose delivery capability to the user. For example, the control mechanisms may be utilized with fill-at-time-of-use syringes, pre-filled syringes, or safety syringes having integrated needle retraction or needle sheathing safety features, or a combination thereof. Further, dose control mechanisms according to the teachings of this disclosure may be utilized with conventional syringes, as well as so-called mixing syringes. For example, the dose control mechanisms may be incorporated into syringes such as those disclosed in U.S. patent application Ser. No. 13/566,079, which is incorporated herein by reference for all disclosed therein.

Examples of such syringes which incorporate the novel dose control mechanisms are provided below. By employing the respective plunger 14 and, optionally, the dose markings 14A and guide markings 20B, the user can control the volumetric dose quantities within the syringe that is desired for delivery to the patient. The plunger dose markings 14A may correspond to the relevant dose amounts desired by the user. The user may initially utilize the plunger, such as by axially depressing the button or rotating the plunger, to identify and select the desired dose amount by aligning the desired dose marking 14A with the guide marking 20B. Axial rotation of the plunger 14 causes the plunger 14 to axially translate in the distal direction, which motion is transferred by the above described mechanism to the screw 30. Axial translation of the screw 30 in the distal direction causes drug fluid contained within the drug chamber of the syringe to be dispensed through the needle of the barrel adapter assembly. Once the desired dose has been identified and selected by the user, the remaining amount of drug fluid within the drug chamber is substantially the exact amount desired to be injected. Syringe may then be injected into the patient for drug delivery. After injection of the needle into the patient, the user may further depress the plunger 14

(and/or the button 12) axially in the distal direction to deliver the drug dose. Because of the novel aspects of the present invention, including the pitch ratio and mechanical stop mechanisms described above, the accuracy of the dose is finely controlled and variability is reduced. In the embodiments of the present invention intended for fill-at-time-of-use syringes, the plunger 14 and screw 30 may initially function in reverse (e.g., axially translate in the proximal direction) to draw-in drug fluid from a vial or container to fill the drug chamber of the syringe. In the embodiments of the present invention intended for retractable or safety syringes, the plunger 14 and screw 30 may function, substantially after the drug dose has been delivered, to initiate or engage a needle retraction or safety mechanism. These embodiments of the present invention are discussed in further detail below with reference to the accompanying figures.

Figure 4A:
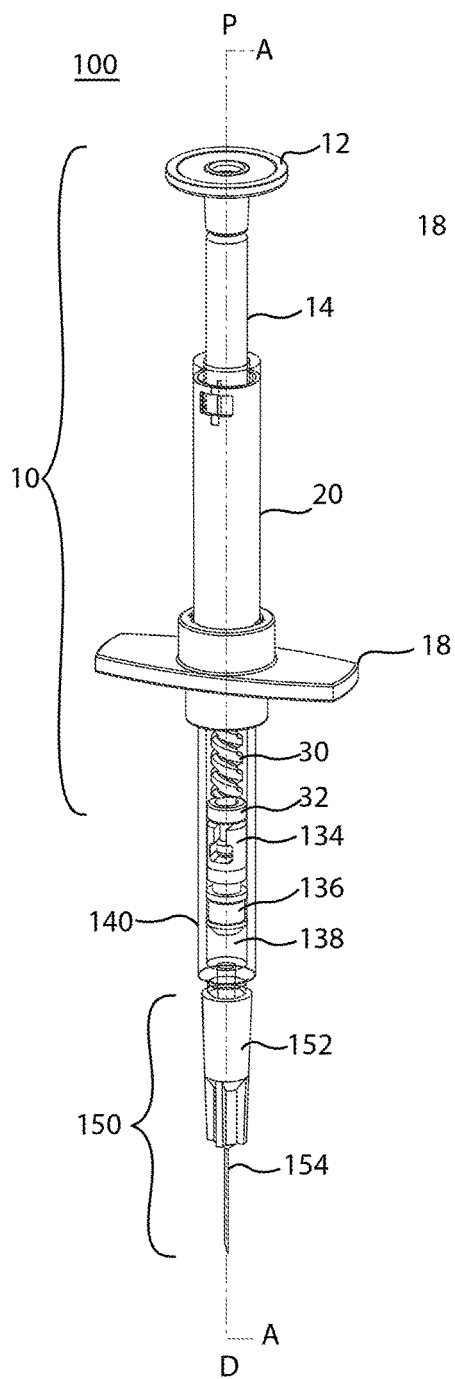
FIG. 4A shows an isometric view of a drug delivery syringe which incorporates a dose control mechanism, according to a second embodiment of the present invention.

FIG. 4A shows an embodiment of the dose control mechanism 10 as a component of an exemplary fill-at-time-of-use drug delivery syringe 100, i.e., syringes which can be drawn back and filled with a drug treatment by the user. As shown, the control mechanism 10 includes a plunger 14, a housing 20, an adapter 18, and a screw 30. The plunger 14 may include a button 12 as a unified or separate component, as described above. Housing 20 may optionally include housing cover 16 at its proximal end, for example, to close the interior of the housing 20 off from the environment and/or to axially align plunger 14 within housing 20. Housing 20 may further include a window 20A, which may be an opening (e.g., an aperture) in the housing or a transmissive, translucent, and/or optically magnifying component. Plunger 14 may include one or more dose markings 14A on the external surface of the plunger 14. Housing 20 may have one or more reference or guide markings 20B, such as at the window 20A, with which to align plunger dose markings 14A. The control mechanism 10 may be attached, mounted, affixed, or otherwise connected at the proximal end of barrel 140 such that at least a portion of the screw 30 resides inside barrel 140.

Figure 4B:
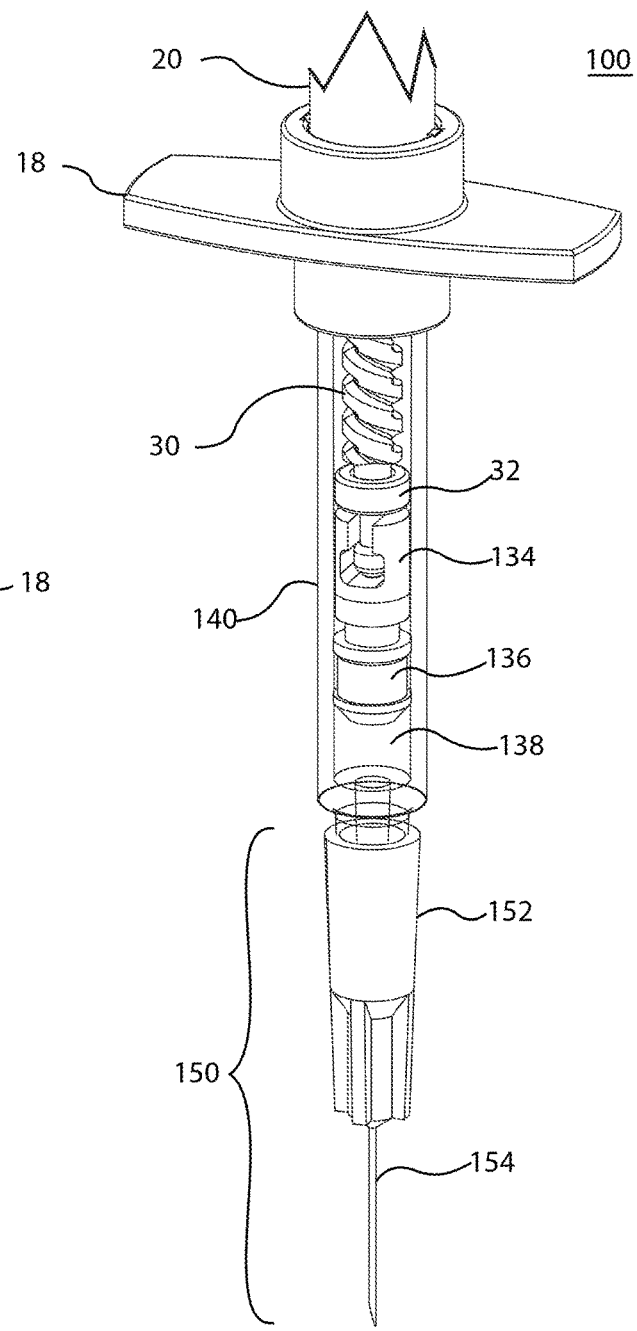
FIG. 4B shows an enlarged isometric view of the distal portion of the drug delivery syringe shown in FIG. 4A.

FIG. 4B shows an enlarged isometric view of the distal portion of the drug delivery syringe shown in FIG. 4A. Screw 30 may be connected to plunger seal 136 either directly or indirectly to drive the axial translation of the plunger seal 136. In the latter configuration, a plunger rod 134 may be utilized between screw 30 and plunger seal 136 to connect those components. The plunger rod 134 may be connected to the screw 30 at, for example, the screw connection 30A aspect. Optionally, a ring 32 near the distal end of the screw 30 may be utilized to facilitate the connection of the screw 30, the plunger rod 134 and the plunger seal 136. The screw connection 30A aspect and the ring are visible in FIGS. 2A, 2B, and 3B. In at least one embodiment, the screw connection 30A aspect is connected to the plunger rod 134 through a radial opening in the plunger rod. Additionally or alternatively, this connection may be a snap-fit connection, an interference-fit connection, or a number of other connection methods known in the industry. In at least one other embodiment, the screw connection aspect is connected to the plunger rod through a proximal opening in the plunger rod such that the screw connection aspect sits within a proximal pocket in the plunger rod. Preferably, the connection between the screw 30 and the plunger seal 136, or screw 30 and plunger rod 134 when a plunger rod is employed, is such that the screw is permitted to axially rotate while the plunger rod and/or the plunger seal remain rotationally fixed. Accordingly, as the plunger 14 and screw 30 of the control mechanism 10 are axially rotated and translated, the motion is relayed to the plunger seal 136 which is also axially translated.

When utilized within a fill-at-time-of-use syringe, the plunger 14 and screw 30 may initially function in reverse (e.g., axially translate in the proximal direction) to draw-in drug fluid from a vial or container to fill the drug chamber 138 of the syringe 100. As described above, the control mechanism 10 may then be utilized by the user to identify and select drug dose for delivery. The user may then inject the needle into the patient for drug delivery. Subsequently, the button 12 and/or plunger 14 may be depressed by the user to cause the plunger 14 and screw 30 to axially translate. Because of the function of the control mechanism and the pitch ratio, any measure of distal translation of the plunger 14 causes only an incremental measure of distal translation of the screw 30, permitting accurate dose delivery control by the user. Axial translation of the screw 30 causes axial translation of the plunger seal 136. This axial motion in the distal direction of the plunger seal 136 forces drug fluid out of drug chamber 138 of barrel 140, through the needle 154 of the barrel adapter assembly 150, for injection and delivery to the patient.

Figure 5A:
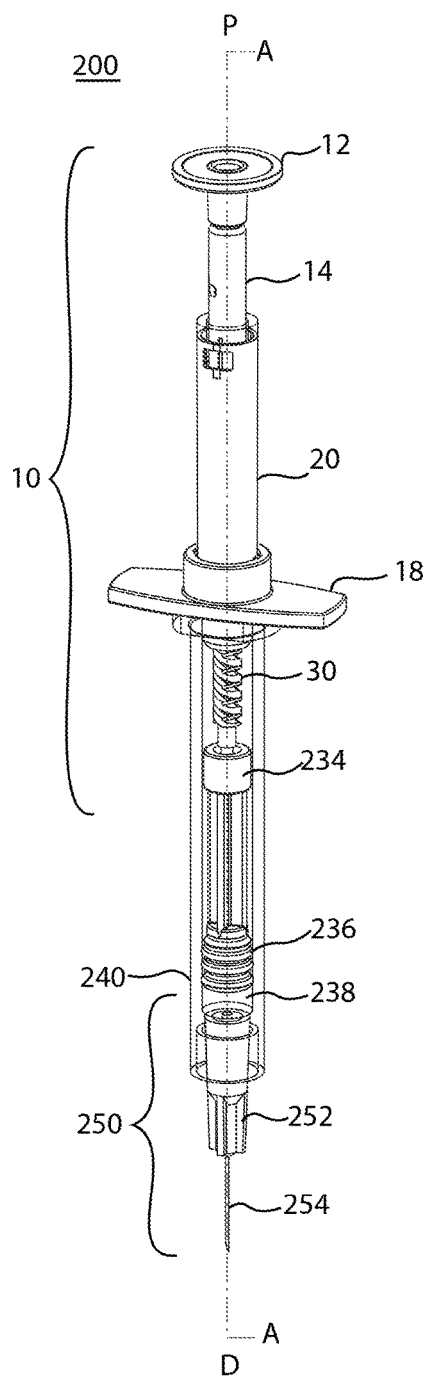
FIG. 5A shows an isometric view of another drug delivery syringe which incorporates a dose control mechanism, according to another embodiment of the present invention.

Similarly, the novel control mechanisms of the present invention may be utilized with pre-filled syringes, i.e., syringes which are filled with a drug treatment by the manufacturer and ready for injection by the user. FIG. 5A shows an embodiment of the dose control mechanism 10 as a component of an exemplary pre-filled drug delivery syringe 200. As shown, the control mechanism 10 includes a plunger 14, a housing 20, an adapter 18, and a screw 30. The plunger 14 may include a button 12 as a unified or separate component, as described above. Housing 20 may optionally include housing cover 16 at its proximal end, for example, to close the interior of the housing 20 off from the environment, to axially align plunger 14 within housing 20, and/or to prevent the plunger 14 being accidently removed by the user/clinician. Housing 20 may further include a window 20A, which may be an opening (e.g., an aperture) in the housing or a transmissive or translucent component. Plunger 14 may include one or more dose markings 14A on the external surface of the plunger 14. Housing 20 may have one or more reference or guide markings 20B, such as at the window 20A, with which to align or view plunger dose markings 14A. The control mechanism 10 may be attached, mounted, affixed, or otherwise connected at the proximal end of barrel 140 such that at least a portion of the screw 30 resides inside barrel 140.

Figure 5B:
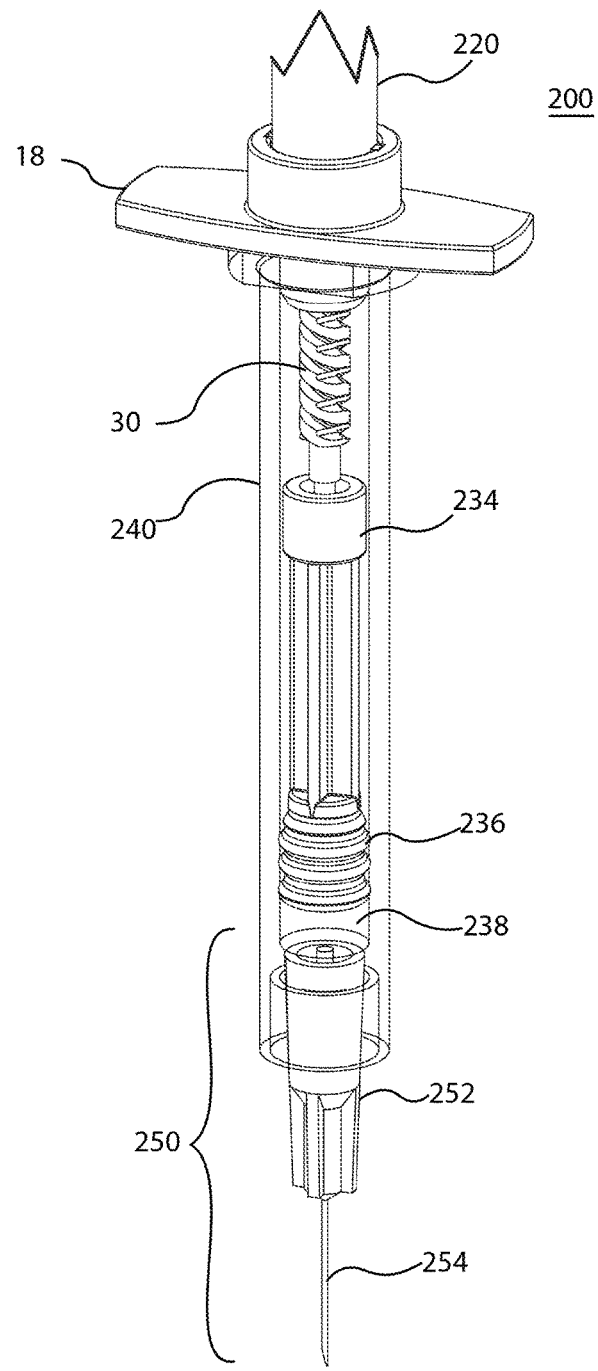
FIG. 5B shows an enlarged isometric view of the distal portion of the drug delivery syringe shown in FIG. 5A.

FIG. 5B shows an enlarged isometric view of the distal portion of the drug delivery syringe shown in FIG. 5A. Screw 30 may be connected to plunger seal 236 either directly or indirectly to drive the axial translation of the plunger seal 236. In the latter configuration, a plunger rod 234 may be utilized between screw 30 and plunger seal 236 to connect those components. The plunger rod 234 may be connected to the screw 30 at, for example, the screw connection 30A aspect. In at least one embodiment, the screw connection aspect is connected to the plunger rod through a proximal opening in the plunger rod such that the screw connection aspect sits within a proximal pocket in the plunger rod. Additionally or alternatively, this connection may be a snap-fit connection, an interference-fit connection, or a number of other connection methods known in the industry. In at least one embodiment, as is described further below with reference to FIGS. 7A-7D, the screw, screw connection aspect, and plunger rod are configured to be readily connectable after the drug chamber has been filled with a drug fluid and the plunger seal and plunger rod have been inserted into the proximal end of the barrel. Preferably, the connection between the screw 30 and the plunger seal 236, or screw 30 and plunger rod 234 when a plunger rod is employed, is such that the screw is permitted to axially rotate while the plunger rod and/or the plunger seal remain rotationally fixed. Accordingly, as the plunger 14 and screw 30 of the control mechanism 10 are axially rotated and translated, the motion is relayed to the plunger seal 236 which is also axially translated. When utilized within a pre-filled syringe, the control mechanism 10 is generally attached to the barrel 240 after the drug chamber 238 of barrel 240 has been filled with a drug fluid. This is often desired so that the syringe 200 may be filled and assembled in standard pharmaceutical fill-finish process lines. Once the syringe 200 has been filled and assembled, the control mechanism 10 may be utilized by the user to identify and set the selected drug dose for delivery. The user may then inject the needle into the patient for drug delivery. Subsequently, the button 12 and/or plunger 14 may be depressed by the user to cause the plunger 14 and screw 30 to axially translate. Because of the function of the control mechanism and the pitch ratio, any measure of distal translation of the plunger 14 causes only an incremental measure of distal translation of the screw 30, permitting accurate dose delivery control by the user. Axial translation of the screw 30 causes axial translation of the plunger seal 236. This axial motion in the distal direction of the plunger seal 236 forces drug fluid out of drug chamber 238 of barrel 240, through the needle 254 of the barrel adapter assembly 250, for injection and delivery to the patient.

Figure 6A:
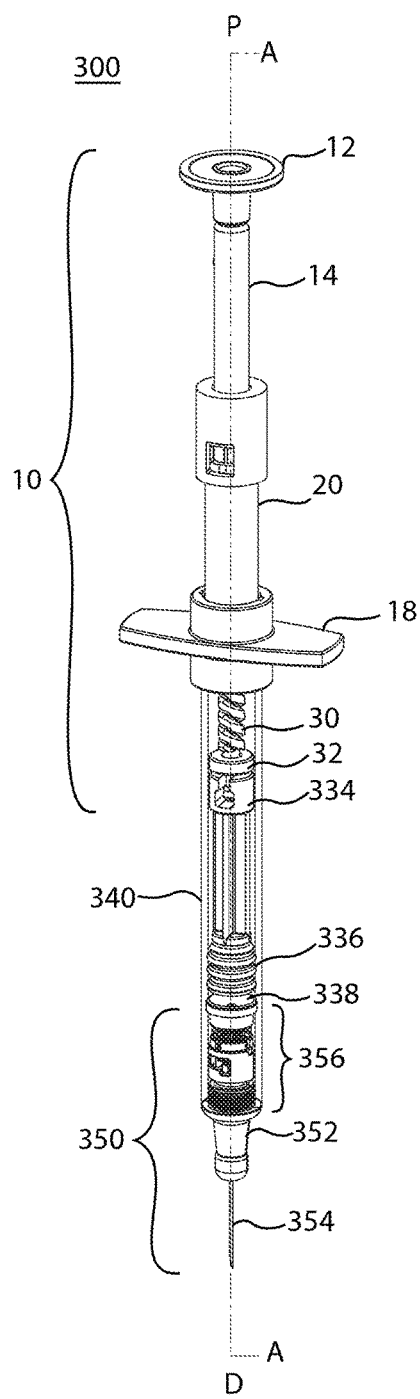
FIG. 6A shows an isometric view of yet another drug delivery syringe which incorporates a dose control mechanism, according to another embodiment of the present invention.

Furthermore, the novel control mechanisms of the present invention may be utilized with safety syringes, such as retractable needle safety syringes (i.e., syringes which incorporate needle safety mechanisms). FIG. 6A shows an embodiment of the dose control mechanism 10 as a component of an exemplary retractable drug delivery syringe 300. As shown, the control mechanism 10 includes a plunger 14, a housing 20, an adapter 18, and a screw 30. The plunger 14 may include a button 12 as a unified or separate component, as described above. Housing 20 may optionally include housing cover 16 at its proximal end, for example, to close the interior of the housing 20 off from the environment, to axially align plunger 14 within housing 20, and/or to prevent accidental removal of plunger 14. Housing 20 may further include a window 20A, which may be an opening (e.g., an aperture) in the housing or a transmissive, translucent, and/or a component providing optical magnification. Plunger 14 may include one or more dose markings 14A on the external surface of the plunger 14. Housing 20 may have one or more reference or guide markings 20B, such as at the window 20A, with which to align or view plunger dose markings 14A. The control mechanism 10 may be attached, mounted, affixed, or otherwise connected at the proximal end of barrel 140 such that at least a portion of the screw 30 resides inside barrel 140.

Figure 6B:
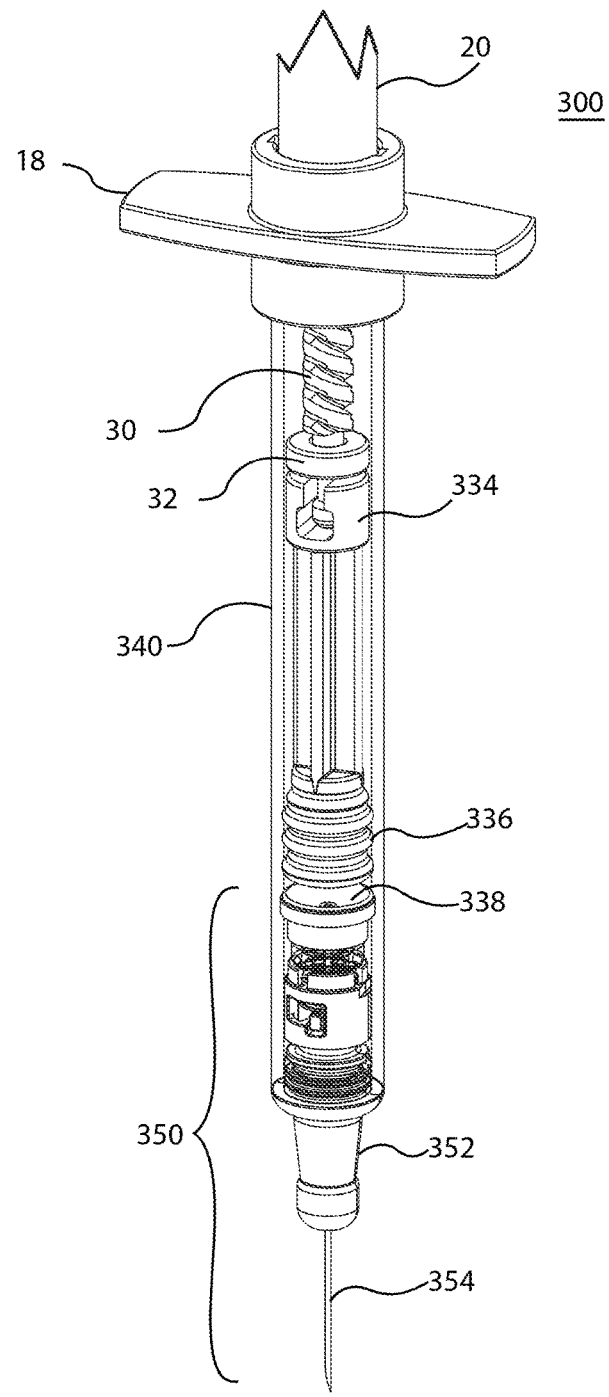
FIG. 6B shows an enlarged isometric view of the distal portion of the drug delivery syringe shown in FIG. 6A.

FIG. 6B shows an enlarged isometric view of the distal portion of the drug delivery syringe shown in FIG. 6A. Screw 30 may be connected to plunger seal 336 either directly or indirectly to drive the axial translation of the plunger seal 336. In the latter configuration, a plunger rod 334 may be utilized between screw 30 and plunger seal 336 to connect those components. The plunger rod 334 may be connected to the screw 30 at, for example, the screw connection 30A aspect. The screw connection aspect may be connected to the plunger rod in the configuration described above with reference to FIGS. 4A and 4B, in the configuration described above with reference to FIGS. 5A and 5B, or any number of other connection methods known in the industry. Preferably, the connection between the screw 30 and the plunger seal 336, or screw 30 and plunger rod 334 when a plunger rod is employed, is such that the screw is permitted to axially rotate while the plunger rod and/or the plunger seal remain rotationally fixed. Accordingly, as the plunger 14 and screw 30 of the control mechanism 10 are axially rotated and translated, the motion is relayed to the plunger seal 336 which is also axially translated. The plunger 14 and screw 30 may function, substantially after the drug dose has been delivered, to initiate or engage a needle retraction or safety mechanism.

When utilized within a safety syringe, such as a retractable needle safety syringe, the plunger 14 of the control mechanism 10 is capable of engaging or initiating a needle safety mechanism. Suitably, the needle safety mechanism is facilitated by a biasing member such as a spring, elastic or other member capable of storing and releasing energy to facilitate needle retraction, needle sheathing, or any other method of protecting the user from accidental needle stick injuries. It will be appreciated that the safety syringe may comprise any needle safety mechanism, such as a needle retraction safety mechanism or needle sheathing safety mechanism, which is operable with the control mechanisms and syringes disclosed herein. By way of example, the needle safety mechanism may be a needle retraction safety mechanism as described in International Publication WO2006/119570, International Publication WO2006/108243, International Publication WO2009/003234, International Publication WO2011/075760, and/or U.S. Pat. No. 8,702,653, although without limitation thereto. In at least one embodiment of the present invention, syringe 300 is a needle retraction safety syringe and incorporates the needle retraction safety mechanism 356 as disclosed in U.S. Pat. No. 8,702,653.

Such a needle retraction safety mechanism 356 may be assembled to the syringe barrel 340, for example as part of the barrel adapter assembly 350, through the distal end of the barrel 340. The control mechanism 10 is generally attached to the barrel 340 after the drug chamber 338 of barrel 340 has been filled with a drug fluid. This is often desired so that the syringe 300 may be filled and assembled in standard pharmaceutical fill-finish process lines. Once the syringe 300 has been filled and assembled, the control mechanism 10 may be utilized by the user to identify and set drug dose for delivery. The user may then inject the needle into the patient for drug delivery. Subsequently, the button 12 and/or plunger 14 may be depressed by the user to cause the plunger 14 and screw 30 to axially translate. Because of the function of the control mechanism and the pitch ratio, any measure of distal translation of the plunger 14 causes only an incremental measure of distal translation of the screw 30, permitting accurate dose delivery control by the user. Axial translation of the screw 30 causes axial translation of the plunger seal 336. This axial motion in the distal direction of the plunger seal 336 forces drug fluid out of drug chamber 338 of barrel 340, through the needle 354 of the barrel adapter assembly 350, for injection and delivery to the patient. At the end of drug delivery, the plunger seal 336 is caused to contact a component of the needle retraction safety mechanism 356 to initiate the retraction mechanism thereby causing retraction of the needle 354 into the barrel 340 of syringe 300. The screw 30 and other components or the control mechanism 10 may be configured or adjusted to permit this additional range of axial translation in the distal direction after the desired drug dose has been delivered. As the needle 354 is then retracted into the barrel 340 of syringe 300, components of the needle retraction safety mechanism 356 bear and push against plunger seal 356 in the proximal direction. As that retraction force is continued, the user may control the rate of needle retraction by controllably reducing the force they apply on the button 12 and/or plunger 14 as the screw 30 and plunger 14 move in the proximal direction. The needle retraction safety mechanism 356 therefore provides a number of additionally desirable features to the novel syringes of the present invention.

As would readily be appreciated by one having ordinary skill in the art, the barrel adapter assembly may be attached, mounted, affixed, or otherwise connected to the distal end of the barrel by a number of known methods. For example, a luer connection may be utilized to connect the barrel adapter assembly to the syringe barrel. Luer connection systems are a standard way of attaching syringes, catheters, hubbed needles, IV tubes, and the like to each other. Luer connections consist of conical/tubular male and female interlocking components slightly tapered to hold together better. Luer connections can either be a "luer slip", as shown in FIGS. 4A and 4B, which are luer connections with a simple pressure or twist fit; or luer connections be a "luer lock", as shown in FIGS. 5A and 5B, which can have an additional outer rim of threading allowing them to be more secure. Alternatively, the connection may be facilitated by a barrel adapter connection. By way of example, the barrel adapter connection may be as described in International Publication WO2011/137488 and/or U.S. Pat. No. 8,702,653, although without limitation thereto. Luer connections, interference fit connections, barrel adapter connections, or any number of other known connections may be utilized to attach the barrel adapter assembly to the barrel while remaining within the breadth and scope of the present invention. Regardless of the type of barrel adapter assembly utilized, the barrel adapter assembly generally comprises of a barrel tip 152, 252, 352 and a needle 154, 254, 354, respectively. In some configurations, the barrel tip 152, 252, 352 may be a pre-formed aspect at the distal end of the barrel. Alternatively, the barrel tip 152, 252, 352 may be a separate component that is attached at the distal end of the barrel. The needle 154, 254, 354 may be any type of fluid conduit including, for example, a flexible cannula or a rigid needle, and may be made of any number of materials, including stainless steel. The type of connections described herein can be utilized regardless of the type of syringe with which they are shown. For clarity, the luer slip connection shown with the fill-at-time-of-use syringe in FIGS. 4A and 4B may be utilized with the pre-filled syringe in FIGS. 5A and 5B, or any other type of connection may be used with any other type of syringe described herein.

It will be appreciated from the foregoing that the novel dose control mechanisms and syringes disclosed herein provide an efficient and easily operated system for the accurate dose setting and delivery of drug treatments. Such devices are safe and easy to use, and are aesthetically and ergonomically appealing for clinical practitioners. The embodiments of the present invention overcome the challenges faced with the use of conventional syringes for the dosing and delivery of low-volume treatments by utilizing novel dose control mechanisms. The novel dose control mechanisms permit the user to accurately read and dose the desired volume of drug treatment for delivery to the patient. These devices permit the user to have a normal range of thumb travel, as they may otherwise expect with a conventional syringe, but transform that range of thumb travel to a very finite (e.g., smaller or incremental) range of plunger seal travel. This relationship allows the user to utilize the syringe without additional training, but with the significant benefit of incremental, low-volume dose control.

Assembly and/or manufacturing of control mechanism 10, syringe 100, syringe 200, or syringe 300, or any of the individual components may utilize a number of known materials and methodologies in the art. For example, a number of known cleaning fluids such as isopropyl alcohol and hexane may be used to clean the components and/or the devices. A number of known adhesives or glues may similarly be employed in the manufacturing process. For example, a glue or adhesive may be utilized to connect the distal end of the housing 20 to the proximal end of adapter 18. Similarly, a glue or adhesive may be utilized to connect the distal end of adapter 18 to the proximal end of the barrel. Additionally, known siliconization fluids and processes may be employed during the manufacture of the novel components and devices. Furthermore, known sterilization processes may be employed at one or more of the manufacturing or assembly stages to ensure the sterility of the final product.

In one embodiment, a method of assembling the control mechanism includes the steps of:
(i) threading a fine pitch screw at least partially through a fine pitch nut of an adapter;
(ii) threading a plunger, the plunger having a coarse pitch screw on its outer surface and an annular space within its inner surface, at least partially through an interior axial pass-through of housing, wherein the housing interior has a corresponding coarse pitch guide;
(iii) inserting at least a proximal portion of the screw into the annular space of the plunger through a distal portion of the plunger; and
(iv) attaching the outer distal portion of the housing to a proximal aspect of the adapter.

Additionally, the plunger may include a button at its proximal end. The button may be a pre-formed aspect of the plunger or may be a separate component from the plunger. Preferably, the button is a separate component attached to plunger by, for example, snap-fit. Similarly, the housing may include a housing cover at its proximal end. The housing cover may be a pre-formed aspect of the housing or may be a separate component from the housing. As discussed above, a glue or adhesive may be utilized to affix one or more components of the control mechanism to each other. Alternatively, one or more components of the control mechanism may be a unified component. For example, the housing may be a separate component affixed by a glue to adapter, or the adapter may be a preformed aspect at the distal end of the housing which is glued to the barrel. Similarly, the housing cover may be affixed by a glue to the housing. These components may be sterilized individually or together, and may be assembled in a sterile environment or sterilized after assembly. The barrel may be siliconized prior to or after assembly.

The control mechanism may be utilized as a component of a syringe. In one embodiment, the method of manufacturing a syringe comprising a control mechanism includes the steps of:
(i) mounting a barrel adapter assembly to a distal end of a syringe barrel;
(ii) mounting a plunger seal through a proximal end of the syringe barrel; and
(iii) mounting a control mechanism to the proximal end of the syringe barrel, wherein the control mechanism may rest in contact with the plunger seal.

The method of manufacturing a syringe may further comprise, before the step of (ii) mounting a plunger seal through a proximal end of the syringe barrel, the step of: filling the barrel at least partially with a fluid substance. Step (iii) may further require the step of connecting a screw connection aspect of a screw of the control mechanism directly to the plunger or indirectly through a plunger rod which is connected at the proximal end of the plunger seal. The connection between the plunger rod and the plunger seal may be any number of connections including, but not limited to, screw-type connection, snap-fit connections, interference connections, capture connections, and the like. In at least one embodiment, the screw connection aspect is connected to the plunger rod through a radial opening or a proximal opening in the plunger rod such that the screw connection aspect sits within a proximal pocket in the plunger rod. Additionally or alternatively, this connection may be a snap-fit connection, an interference-fit connection, or a number of other connection methods known in the industry. Preferably, the connection between the screw and the plunger seal, or between the screw and plunger rod when a plunger rod is employed, is such that the screw is permitted to axially rotate while the plunger rod and/or the plunger seal remain rotationally fixed.

Figures 7A, 7B:
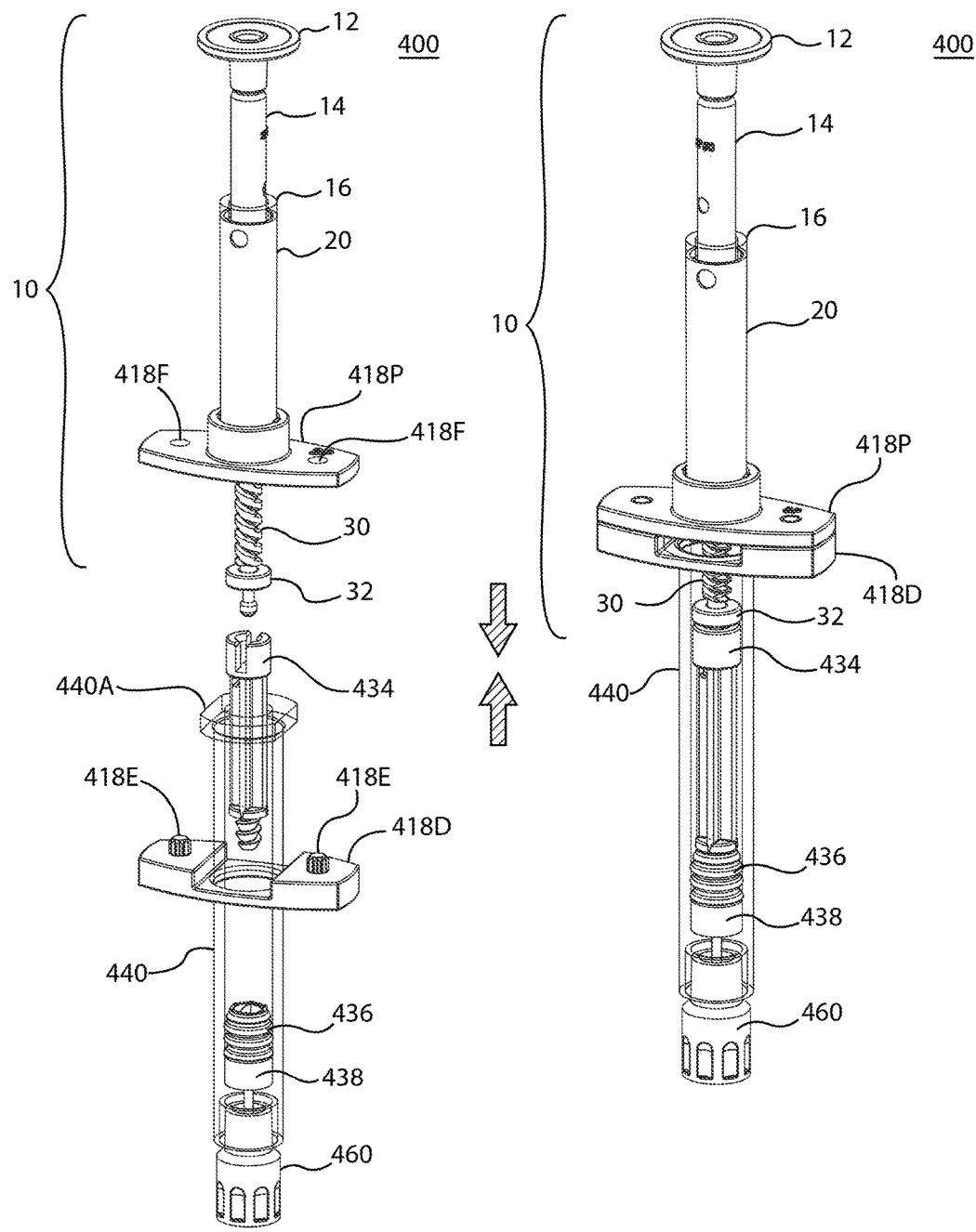
FIG. 7A shows an isometric view of an initial assembly stage of a pre-filled drug delivery syringe which incorporates a dose control mechanism, according to at least one embodiment of the present invention.
FIG. 7B shows an isometric view of the pre-filled drug delivery syringe shown in FIG. 7A after it has been assembled.

One preferred method of manufacturing a syringe having a dose control mechanism, according to one embodiment of the present invention, is described herein with reference to FIGS. 7A-7D. FIG. 7A shows a pre-filled syringe, such as that described with reference to FIGS. 5A-5B above, wherein the adapter is a two-component adapter having a proximal adapter portion 418P and a distal adapter portion 418D. Proximal adapter portion 418P has one or more connection prongs 418E and distal adapter portion 418D has corresponding connection ports 418F. When forced together, connection prongs 418E and corresponding connection ports 418F merge, mate, or otherwise connect to unite the two portions of the adapter 418P, 418D. Initially, a cap 460 may be connected to the distal end of barrel 440 of syringe 400. The distal adapter portion 418D may be slidably mounted to the exterior of the barrel. The interior of the barrel 440, i.e. the drug chamber 438, may be filled with a drug fluid or substance through the open proximal end of the barrel. The plunger seal 436 may be mounted into the barrel through the proximal end such that is in contact with the fluid. The optional plunger rod 434 may be connected to the plunger seal 436 prior to, or after, insertion of the plunger seal 436 into the barrel 440. These steps may be performed in a sterile environment to maintain the container integrity and sterility of the drug treatment.

Figures 7C, 7D:
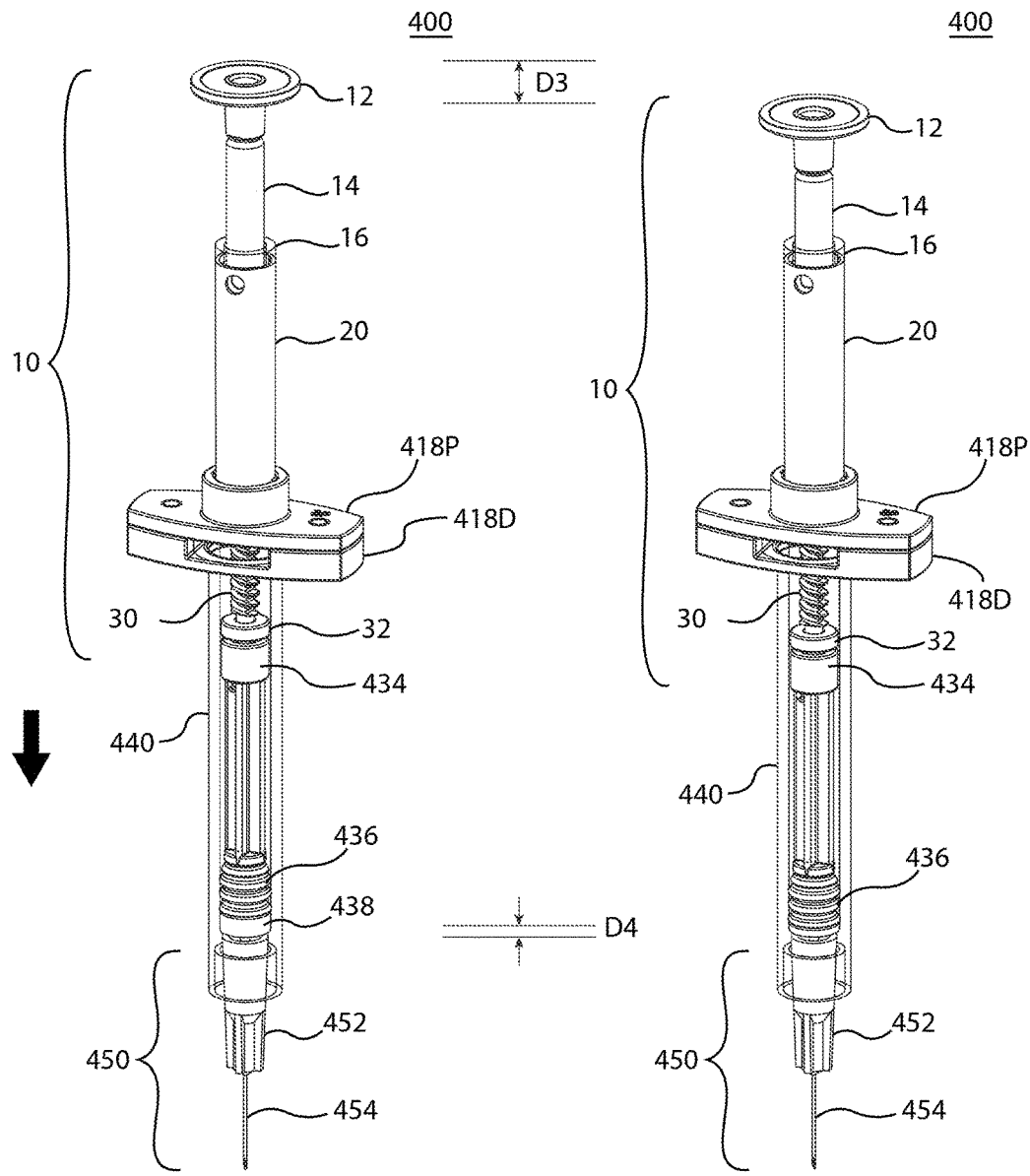
FIG. 7C shows an isometric view of the pre-filled drug delivery syringe shown in FIG. 7A in a ready-to-inject stage of operation.
FIG. 7D shows an isometric view of the pre-filled drug delivery syringe shown in FIG. 7A in an end-of-dose stage of operation

The remainder of the syringe may then be assembled in a non-sterile or sterile environment. The screw, as a component of the control mechanism, may then be connected to the plunger seal or to the plunger rod when a plunger rod is employed. The distal adapter portion 418D may then be slid in the proximal direction along the exterior of the barrel to connect to the proximal adapter portion 418P as described above. The connection between the distal adapter portion 418D and the proximal adapter portion 418P may capture a barrel flange 440A aspect of the barrel 440 in order to retain the control mechanism 10 at the proximal end of the barrel 440. Various glues or adhesives may be utilized to ensure that such components and connections are retained in position during assembly, filling, manufacturing, transportation, storage, and operation of the novel devices of the present invention. The final assembly of the syringe, such as in the pre-filled syringe 400, may appear as shown in FIG. 7B. This type of pre-filled syringe may be utilized when, for example, a syringe is to be filled with a standard amount of drug fluid by a pharmaceutical company or contract drug filler, when the drug dose is variably selectable by the user, when the needle length is variably selectable by the user, or in a number of other situations. FIG. 7C shows the pre-filled syringe with a selectable needle that is attached via a luer lock connection, as described above. In such a scenario, the syringe may be held such that the distal end of the syringe is pointed upwards. The cap 460 (shown in FIG. 7B) may be removed and replaced by a barrel adapter assembly 450. The barrel adapter assembly 450 includes a barrel tip 452 and needle 454 which may be selected by the user and attached to the pre-filled syringe just prior to use. The drug dose may be identified and selected by the user, as described above. Comparison of the pre-filled syringe 400 in FIGS. 7C and 7D clarifies the differences in the pre-filled syringe just prior to, and after, injection and delivery of the drug dose to the patient. Because of the pitch ratio between the plunger 14 and the screw 30, screw 30 is caused to axially translated in the distal direction only incrementally or to a lesser distance when plunger 14 is depressed or axially translated in the distal direction (i.e., in the direction of solid arrow in FIGS. 7C and 7D). This difference in axial translation distance between plunger 14 and screw 30 is visible by comparing distances D3 and D4 in FIGS. 7C and 7D. D3 is the distance that plunger 14 axially translates while D4 is the fractional distance that screw 30 axially translates.

Figure 8A:
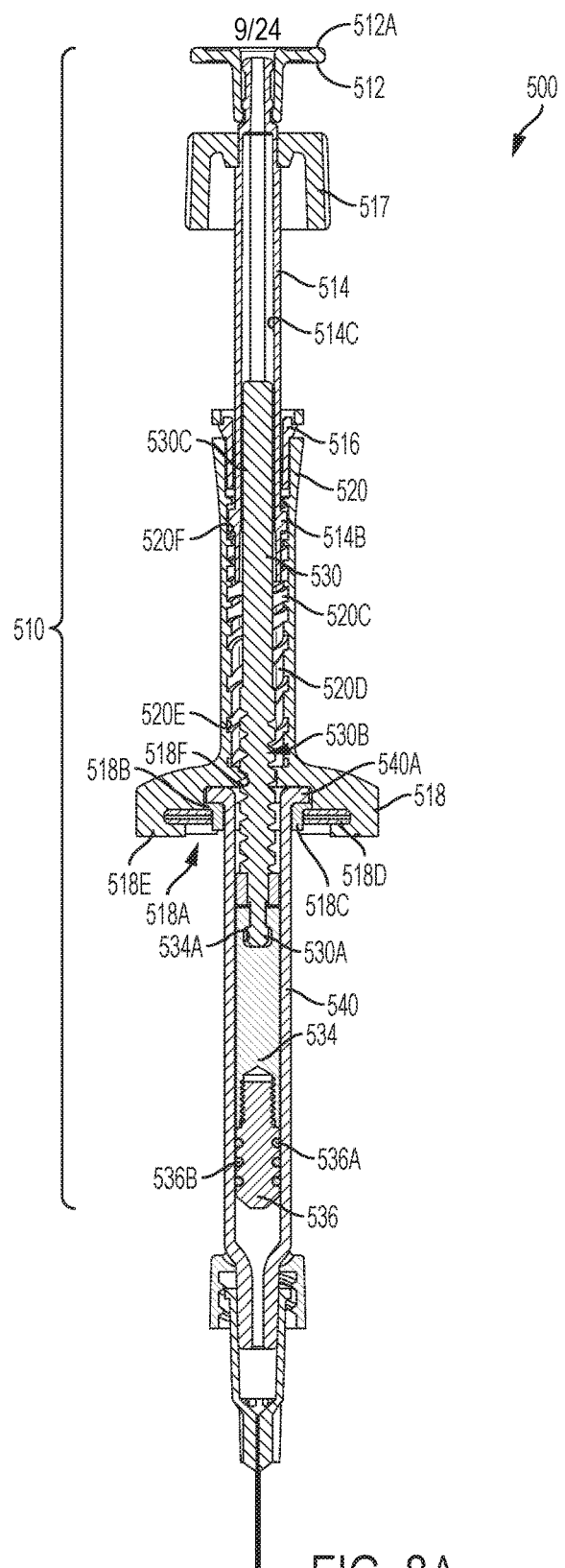
FIG. 8A shows a cross-sectional view of an alternate design of a dose control mechanism as the components may appear in a ready-to-inject stage of operation.
Figure 8B:
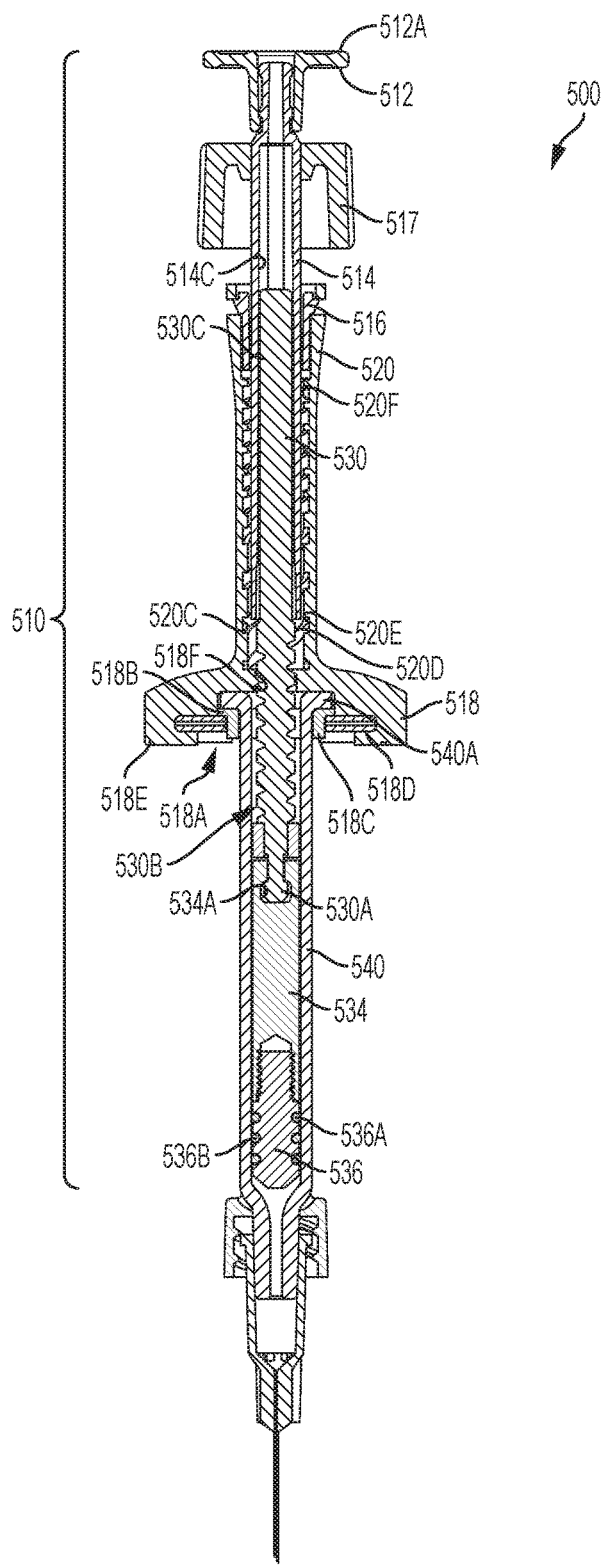
FIG. 8B shows a cross-sectional view of the dose control mechanism shown in FIG. 8A as the components may appear in a ready-to-inject stage of operation.
Figure 8C:
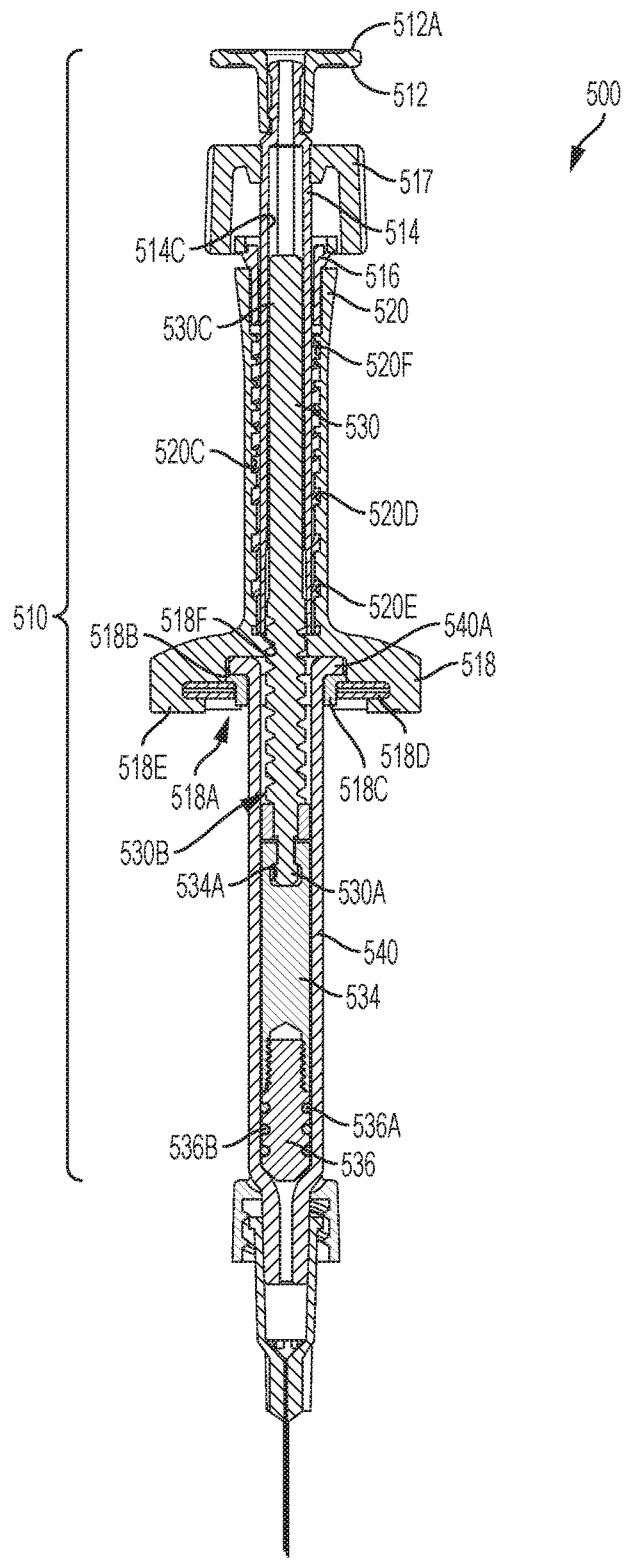
FIG. 8C shows a cross-sectional view of the dose control mechanism shown in FIG. 8A as the components may appear in an end-of-dose stage of operation.

Yet another embodiment of a syringe 500 incorporating a dose control mechanism 510 is illustrated in FIGS. 8A-8C. The embodiment of FIGS. 8A-8C offers advantages of both the dose control mechanisms of the earlier-described embodiments, and the advantages of conventional syringes, as will be explained below. FIGS. 8A, 8B, and 8C show cross-sectional views of the dose control mechanism in a ready-to-inject stage, partially injected stage, and in an end-of-dose stage, respectively, while FIGS. 9A and 9B illustrate partially exploded views of the dose control mechanism 510 of this embodiment.

As with the earlier-disclosed embodiments, the dose control mechanism 510 for a syringe 500 includes a plunger 514, a housing 520, an adapter 518, and a screw 530. The housing 520 has a substantially cylindrical axial pass-through within which the substantially cylindrical plunger 514 may at least partially reside. The distal end of the housing 520 includes the adapter 518. The housing 520 and the adapter 518 of this embodiment are formed as a unitary structure, the adapter 518 presenting a finger flange for engagement by a user during operation. It will be noted, however, that the housing 520 and adapter 518 may be separately formed, as illustrated with regard to other embodiments.

The adapter 518 may couple the dose control mechanism 510 to the barrel 540 of a syringe 500 by any appropriate structure. In the illustrated embodiment, adapter 518 is coupled to the barrel 540 by way of an insert 518A, which is received in a laterally extending opening 518B in the adapter 518. While the insert may be of any appropriate design, the illustrated insert 518A includes a gasket 518C and a positioning insert 518D. The barrel 540 of the syringe 500 is received within an opening in the gasket 518C, with the barrel flange 540A disposed along an upper surface of the gasket 518C. The gasket 518C and the barrel 540 are inserted through an opening in the positioning insert 518D that may be slidably received within the laterally extending opening 518B of the adapter 518; laterally extending flanges 518E may serve to maintain the insert 518A and the associated barrel 540 in position. Thus, in assembly, the barrel 540 may be inserted into openings in the gasket 518C and positioning insert 518D, and then slide into position within the laterally extending opening 518B in the adapter 518.

As with the above embodiments, the screw 530 may be coupled to a plunger rod 534 in any appropriate manner, either directly or indirectly. For example, as with the embodiments of FIGS. 1A-7D, a connection aspect 530A of the screw 530 may be received within a recess 534A at the proximal end of the plunger rod 534. In the illustrated embodiment, the distal end of the plunger rod 534 is coupled to a plunger seal 536 by a screw connection, although alternate connections known in the art may be provided. Likewise, the plunger seal 536 may be of any appropriate design. For example, in the illustrated embodiment a plurality of ring seals 536A are disposed within a corresponding plurality of peripheral recesses 536B of the plunger seal 536.

Housing 520 may optionally include housing cover 516 at its proximal end, for example, to close the interior of the housing 520 off from the environment and/or to axially align plunger 514 within housing 520, and to prevent removal of the plunger rod by functioning as a mechanical stop.

Housing 520 may further include a dosage reference arrangement. For example, as discussed in greater detail above, the housing 520 may be provided with a window 520A (see FIG. 9B) to permit the user to view the location of the plunger 514 within housing 520 by viewing the location of one or more dose markings on the external surface of the plunger 514. While not illustrated in detail in this embodiment, those of skill in the art will appreciate that the same or a similar arrangement may be provided in this embodiment as in the earlier embodiments.

The plunger 514 may include a button 512 presenting a user interface surface 512A for engagement by a user to translate the plunger 514 axially within the housing 520. The button 512 and plunger 514 may be a unitary component, or separate components. For example, button 512 may be a preformed aspect at the proximal end of the plunger 514. Alternatively, button 512 may be a separate component attached to the proximal end of plunger 514 by a snap-fit. In at least one embodiment, the button 512 may be attached to plunger 514, but allowed to rotate freely about the proximal end of plunger 514. In this way, the button 512 may be rotationally fixed relative to the user's/clinician's finger while permitting the plunger 514 to rotate as the plunger translates axially.

The plunger 514 may additionally include a plunger dial 517 that may provide an alternative or additional structure by which to manipulate the plunger 514. In the illustrated embodiment, for example, the plunger dial 517 is secured with the plunger 514. As a result, by rotating the plunger dial 517, a user may directly rotate the plunger 514 as desired. In this way, the plunger dial 517 may be rotated to either draw in medication or administer medication, depending upon which direction the plunger is rotated.

As with the embodiments of FIGS. 1A-7B, the screw 530 is disposed at least partially within an axially extending channel 514C within the plunger 514. As illustrated in FIG. 1B with regard to screw 30 and plunger 14, a proximal length 530C of the screw 530 is axially keyed with the plunger 514 for sliding relative movement in an axial direction. In this way, an axial rotation of the plunger 514 results in an axial rotation of the screw 530. As with the embodiments described above, those of skill in the art will appreciate that the axial keying may be other than as specifically illustrated in FIG. 1B.

As with the earlier-discussed embodiments, a distal length 530B of the screw 530 is externally threaded for complimentary engagement with an internally threaded portion 518F of the adapter 518. As a result, rotation of screw 530, as may result from the rotation of the axially keyed plunger 514, will result in rotation of the screw 530 within the adapter 518. As the axial direction in which the screw 530 translates will be dependent upon the rotational direction of the screw 530, the translation of the associated plunger rod 534 and plunger seal 536 likewise will be dependent upon the rotational direction of the screw 530.

The plunger 514 is received within a longitudinally extending channel 520D within the housing 520. In order to provide axial and rotational movement of the plunger 514 relative to and within the housing 520, the longitudinally extending channel 520D and plunger 514 are coupled by an engaging screw thread arrangement. To this end, one of the longitudinally extending channel 520D and plunger 514 includes a length of thread, while the other of the longitudinally extending channel 520D and the plunger 514 includes at least one thread segment disposed to engage the coarse thread. In the illustrated embodiment, the longitudinally extending channel 520D includes a thread 520C, while the plunger 514 includes a thread segment 514B; in this case, as the thread 520C of the longitudinally extending channel 520D is double threaded, the plunger 514 includes a pair of thread segments 514B.

Those of skill in the art will appreciate, however, that in at least one embodiment, the configuration of engaging screw pitch relative to the plunger 514 and housing 520 may be reversed. In other words, the outer surface of the plunger 514 may include a length of coarse thread, while the longitudinally extending channel 520D includes at least one thread segment disposed to engage the thread of the plunger 514. Those of skill in the art will further appreciate that the thread segment along the inner surface of the longitudinally extending channel 520D may include a segment of a screw thread recess within which the external thread of the plunger 514 may ride as it rotates and translates axially. For the purposes of this disclosure, the term "thread segment" will include both a thread recess that may receive a thread, and a thread that may be received within a thread recess.

According to an aspect of the embodiment of FIGS. 8A-9B, the engagement between the plunger 514 and the housing 520 is provided by way of a variable pitch thread 520C, rather than a uniform coarse pitch thread, as illustrated with regard to the embodiment of FIGS. 1A-3B. In this way, it is possible to more precisely tailor the rotation of the plunger 514 relative to the axial translation of the plunger 514 within the housing 520, and, as a result, the rotation and axial translation of the screw 530 relative to the housing 520. Additionally, this arrangement may allow the user to fill the syringe more easily and quickly.

For the purposes of this disclosure, the term "variable pitch thread" 520C means that the thread includes at least two thread pitches for engagement by the thread segment(s) 514B (see FIG. 9B). A first thread pitch 520E is disposed toward the distal end of the housing 520, while a second thread pitch 520F is disposed proximally within the housing 520 from the first thread pitch 520E.

In this embodiment, the first thread pitch 520E is a coarse pitch thread, as illustrated with regard to the embodiment of FIGS. 1A-3B, while the second thread pitch 520F is a relatively finer pitch than that of the first thread pitch 520E. As a result, as the plunger 514 is rotated and the thread segment 514B engages the first pitch thread 520E, the plunger 514 will move in an axial direction as explained above with regard to the embodiment of FIGS. 1A-3B. In other words, as the user advances the plunger 520 with the thread segments 514B engaging the first thread pitch 520E, the plunger 520 will move axially a greater distance than the keyed, relatively smaller pitch screw 530. Conversely, when the user advances the plunger 520 with the thread segments 514B engaging the second thread pitch 520F, the thread pitches of the plunger 520 and the screw 530 are more closely aligned. As a result, the axial distances traveled by the plunger 520 and the screw 530 will be more closely matched. In this way, when the user moves the plunger 520 in a proximal direction at a relatively constant speed to draw a medication into the barrel 540, medication will initially be drawn slowly into the barrel 540 as the thread segments 514B are disposed in the first thread pitch 520E, and more rapidly when the thread segments 514B are disposed in the second thread pitch 520F. Thus, the variable pitch thread 520C facilitates the more rapid draw of larger volumes of medication than the embodiment of FIGS. 1A-3B. Likewise, when the plunger 520 is depressed to prime the syringe or administer medication, the rate at which the plunger seal 536 moves within the barrel 40 will be dependent upon the location of the thread segments 514B within the variable pitch thread 520C, allowing an initially more rapid prime, with a slower, final delivery of medication. In at least one embodiment, upon completion of the priming step of operation, thread segments 514B are disposed in the first thread pitch 520E of the variable pitch thread 520C. This allows the medicament to be accurately delivered to the target using the mechanical advantages described above with reference to FIGS. 1A-3B.

Turning to FIG. 8A, the syringe 500 is illustrated with the plunger 514 in a full draw position. It will be noted that the thread segment 514B is disposed in the second thread pitch 520F portion of the variable pitch thread 520C. As the plunger 514 is depressed, for example, to prime the syringe 500, the thread segment(s) 514B traverses the second thread pitch 520F of the variable pitch thread 520C, generally moving into the first thread pitch 520E, as illustrated in FIG. 8B. During priming, air is typically expelled from the barrel 540, possibly along with a small amount of medication. It will be appreciated that, as the thread segment 514B enters the first thread pitch 520E, the rotational speed of the screw 530 will decrease for a uniform axial movement of the plunger 514. In this way, the user may accurately prime the syringe 500 to a desired dosage. As the user then depresses the plunger 512 or rotates the plunger dial 517, the primed dosage may be delivered, the thread segment 514B rotating relative to the first thread pitch 520E of the variable pitch thread 520C to provide a rotating movement to the screw 530 for delivery of the medication (see FIG. 8C). In this way, the syringe may be quickly filled and primed. For example, the pitch ratio of the first thread pitch 520E to the adapter nut may be 1:1. Thus, when thread segment 514B is disposed in first thread pitch 520E, axial translation of the plunger seal 536 will be equal to the axial translation of the plunger 512. This allows the syringe to perform as a standard syringe during the filling and priming steps, providing a familiar experience for healthcare professionals. After priming, with thread segments 514B disposed in second thread pitch 520F, the syringe provides for fine control of the volume of medicament administered as described above with reference to FIGS. 1-7B.

It will thus be appreciated by those of skill in the art that the variable pitch thread 520C may thus be tailored to provide a desired rotational, and, therefore, axial movement of the screw 530 for a relatively uniform axial movement of the plunger 512. Further, it will be appreciated that variable pitch thread 520C may include greater than two pitches. For example, the variable pitch thread 520C may include three or more different pitches. The pitch may transition along its entire length, gradually going from one pitch to another, such as gradually transitioning from a coarse pitch to a fine pitch. Further, the variable pitch thread 520C may include a transitional pitch between different pitches, such as a transition pitch between a coarse pitch and a fine pitch.

While FIGS. 8A-9B illustrate a unitarily formed housing 520, it will be appreciated that housing 520 may be constructed of a plurality of components. Those of skill in the art will further appreciate that a housing that includes a plurality of components may not only facilitate manufacturing and assembly, but also enhance the customization options and functionality of the device.

Figure 15:
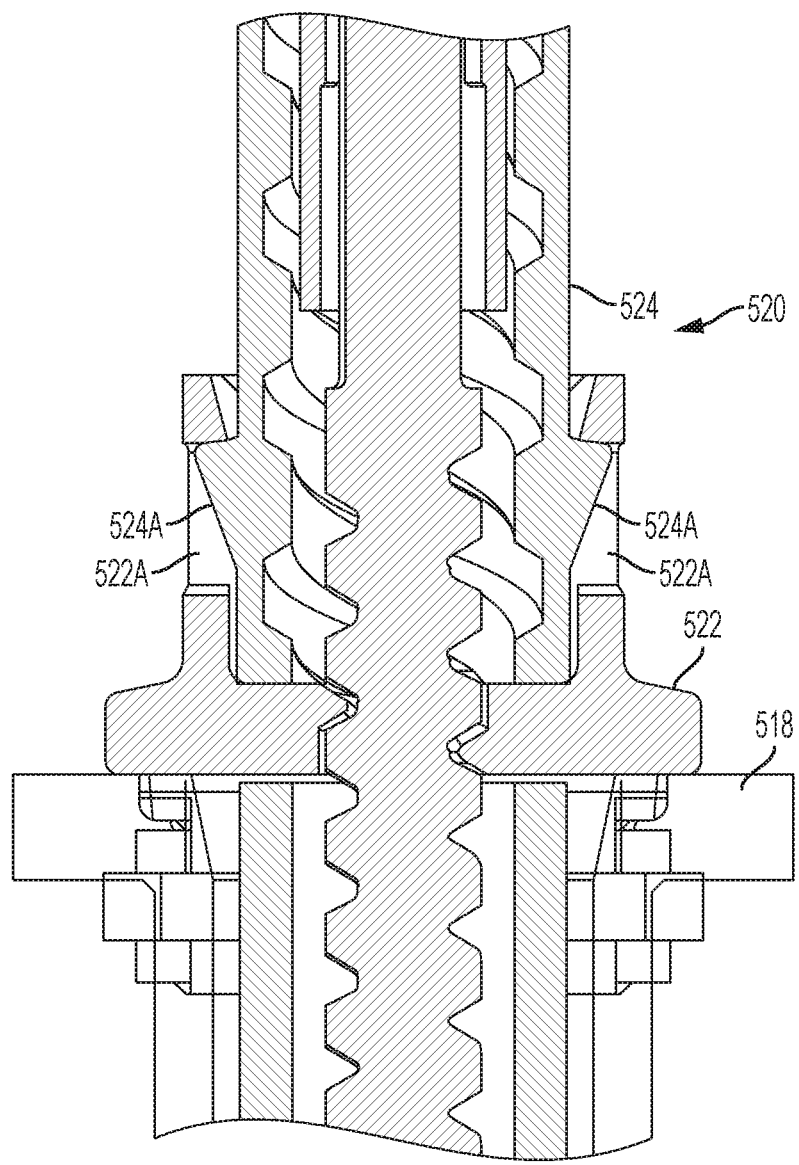
FIG. 15 is an enlarged partial cross-sectional view of an embodiment of an engaging structure between first and second housing sections according to an embodiment of the invention.

For example, the housing 520 may include a lower housing and an upper housing. FIG. 15, for example, shows an exemplary embodiment of the present invention having a housing 520 including a lower housing 522 and an upper housing 524. The lower housing 522 and the upper housing 524 may be assembled together by, for example, including threaded engagement, snap fit, interference fit, hook/prong and window engagement (as shown in cross-sectional FIG. 15) or in a broad range of known methodologies. As shown in FIG. 15, upper housing 524 may include one or more hooks 524A configured to engage one or more windows 522A of lower housing 522. In yet another embodiment the adapter 518 may be formed separately from the lower housing, and assembled to the lower housing 522.

In addition to aiding the manufacture and assembly of these components, bifurcating or even trifurcating the housing 520 into multiple components may have additional functional benefits. For example, the pitch ratios of the individual upper and lower housings 524, 522 may be varied to provide customization options, enabling different accuracy or tuning of dose delivery. Thus, the remaining portions of the device may be uniform structures, regardless of the dose accuracy parameters, but specifically desired dose accuracy of each device may be altered simply by changing or selecting the correct lower and upper housing, along with the interfacing screw-portion of the plunger rod. Accordingly, the device may have substantial customizability while minimizing the components that need to change to meet the exact desired delivery parameters. Further customization may be provided by varying, for example, the pitches of the screw 530 and the internally threaded portion 518F of the adapter 518. In such an arrangement, the adapter 518 may be formed with the lower housing 522 as illustrated, or separately formed from and assembled to the lower housing 522. In this way, the device may be further customized by changing the adapter 518 and the screw 530. Those of skill will appreciate that such an arrangement may provide a wide array of options in customizing the device through the utilization of a number of standardized components that may be mixed and matched to provide the desired delivery parameters. Varying these components can also permit the manufacturer, pharmaceutical company, or user to alter other parameters, such as drug delivery metering, applied forces, and fill volume, since all are dependent at least in part in the selected pitch ratio of these sub-components.

Similarly, the functions of one or more components may further be separated into separate subcomponents. For example, the housing may be further sub-divided such that the upper housing has an inner upper housing and an outer upper housing. The inner upper housing in such an instance could include the screw-threaded portion and interface with the outer upper housing. This may further aid the manufacturing and assembly of the device, and/or improve the range of customization of the devices by replacement of just one sub-component. In this example, the inner upper housing could be readily replaced to alter the screw threading and, accordingly, the accuracy or tuning of drug delivery. Additionally, or alternatively, one or more components could be modified to serve the function of, a function similar to, or supplement the function of, another component described herein. For example, in at least one embodiment the cover 516 may be modified to incorporate a screw-threaded portion that supplements the screw-threaded portion of the upper housing. This may be utilized to provide further axial translation of the plunger and/or may be utilized to provide another portion of the plunger having a varied pitch ratio. In yet another embodiment of the present invention, the threaded cover may be elongated and combined with the inner upper housing such that the cover has a threaded portion that extends substantially the length of the housing or upper housing. Accordingly, the threaded portion of the housing could be a separate component from the housing outer. As a result, the threaded portion may be easily replaced.

Additionally, the threaded portions of the device and/or its sub-components may have any range of thread profiles or cross-sectional configurations. For example, FIGS. 8A-9B illustrate configurations utilizing a rectangular thread profile. The embodiments shown in FIGS. 10A-11B illustrate configurations utilizing a triangular thread profile. The term profile in this sense is meant to refer to the cross-sectional shape of each thread of the screw-threaded portions of the device.

The thread profile or shape may be selected to meet the desired parameters of the functioning device. For example, a triangular thread profile may reduce the glide forces felt by the user and provide a less sticky engagement between the corresponding threaded components. This may be because the engagement surfaces of the corresponding threaded components are altered or occur at a different plane that are perceived by the user as more easily tactile or operated. Additionally, a triangular thread profile may enable more rotations in a smaller axial length. This may provide finer accuracy, tuning, or volume control to the device. Accordingly, while the embodiments of the present invention show a rectangular/squared thread profile or a triangular square profile, a number of thread profiles may be utilized by the present device while remaining within the scope of the presently claimed invention. Similarly, the thread direction may be altered while remaining within the scope of the presently claimed invention.

In the embodiments shown in FIGS. 10A-14, dose control mechanism 610 further includes a housing 620 having at least first and second housings 668, 670 which are adapted for selective telescoping movement relative to one another between a retracted position and an extended position. In this way, the dose control mechanism 610 may be provided in a retracted position, and then extended to draw a medicament into the barrel. In at least one embodiment, the first and second housings 668, 670 may then be translated relative to one another to a primed position from which the medicament may be administered. A first such embodiment is illustrated in FIGS. 10A-11B, and a second such embodiment is illustrated in FIGS. 12A-14. A difference between the first and second such embodiments is the mechanisms by which the relative motion between the first and second housing sections 668, 670 are governed. Accordingly, the same reference numbers are utilized for like components between the two embodiments. Those of skill in the art will appreciate that the illustrated dose control mechanism 600 of FIGS. 12A-12E may be coupled to the barrel of a syringe in a manner similar to the embodiment of FIGS. 10A-10F.

More specifically, in the illustrated embodiments, the second housing section 670 is positioned between the first housing section 668 and the plunger 614. In such an embodiment, the second housing section 670 includes an internal thread 670D—which can be either constant pitch or variable pitch—configured to engage the external thread segments 614B of the plunger 614. The second housing section 670 is configured such that, in a first configuration, it is able to axially translate with respect to the first housing section 668. In a second configuration, the sleeve 670 is fixed in relation to the first housing section 668. As will be explained below, this allows a syringe to be quickly filled and primed in a way that is familiar to the user when the first and second housing sections 668, 670 are moved from the retracted position to the extended position and then to the primed position, while providing accurate dose control during delivery.

Figures 10A, 10B:
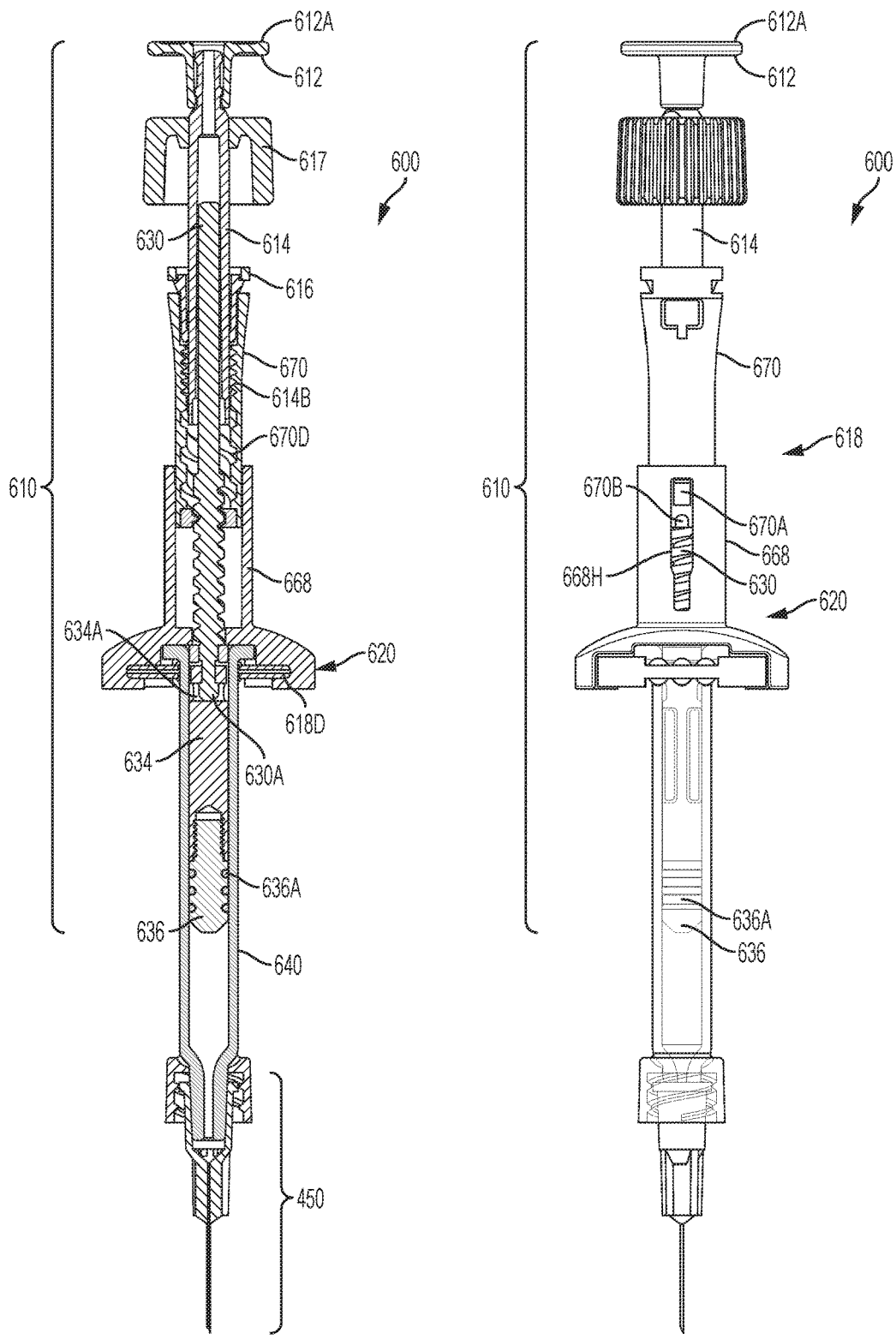
FIG. 10A is a cross-sectional view of a syringe incorporating another embodiment of a dose control mechanism according to the present invention, the housing being illustrated in an extended position.
FIG. 10B is a side elevational view of the syringe of FIG. 10A.
Figure 10C:
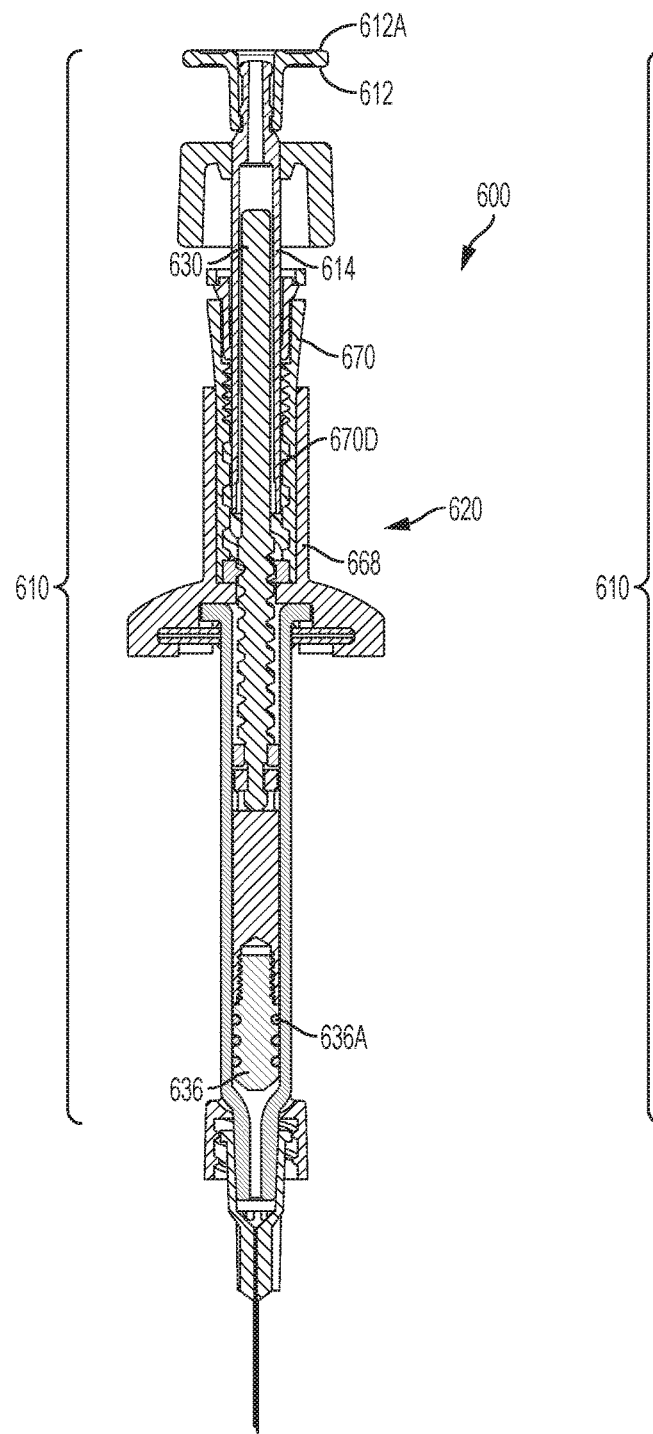
FIG. 10C is a cross-sectional view of the syringe of FIGS. 10A and 10B in a primed position.
Figure 10D:
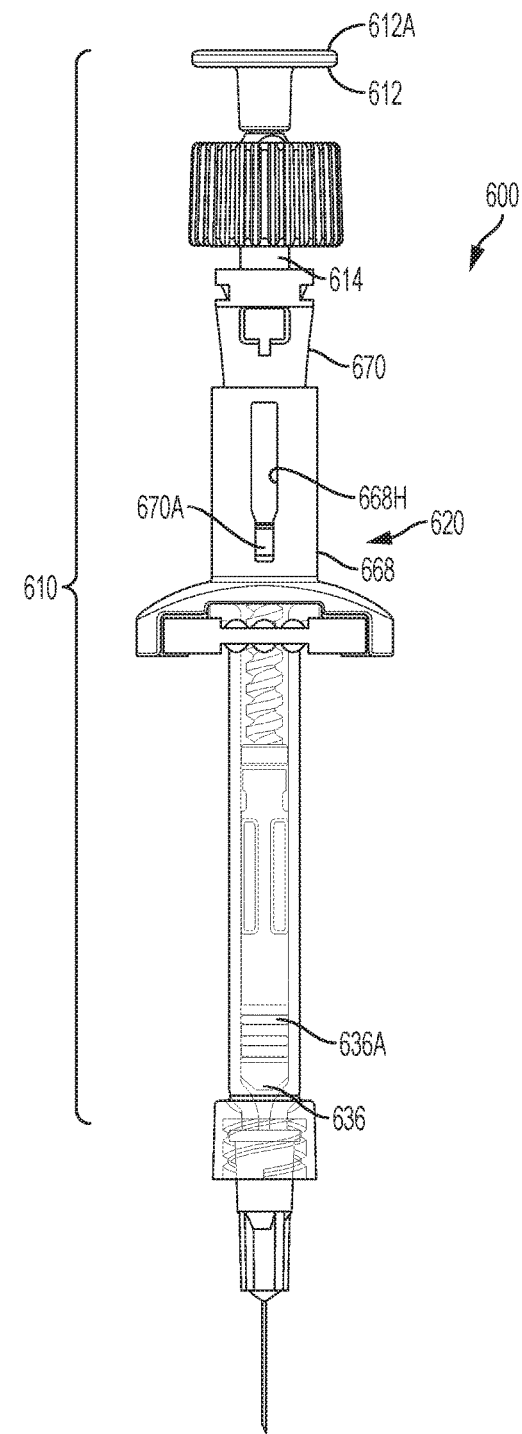
FIG. 10D is a side elevational view of the syringe of FIGS. 10A and 10B in the position illustrated in FIG. 10C.
Figures 10E, 10F:
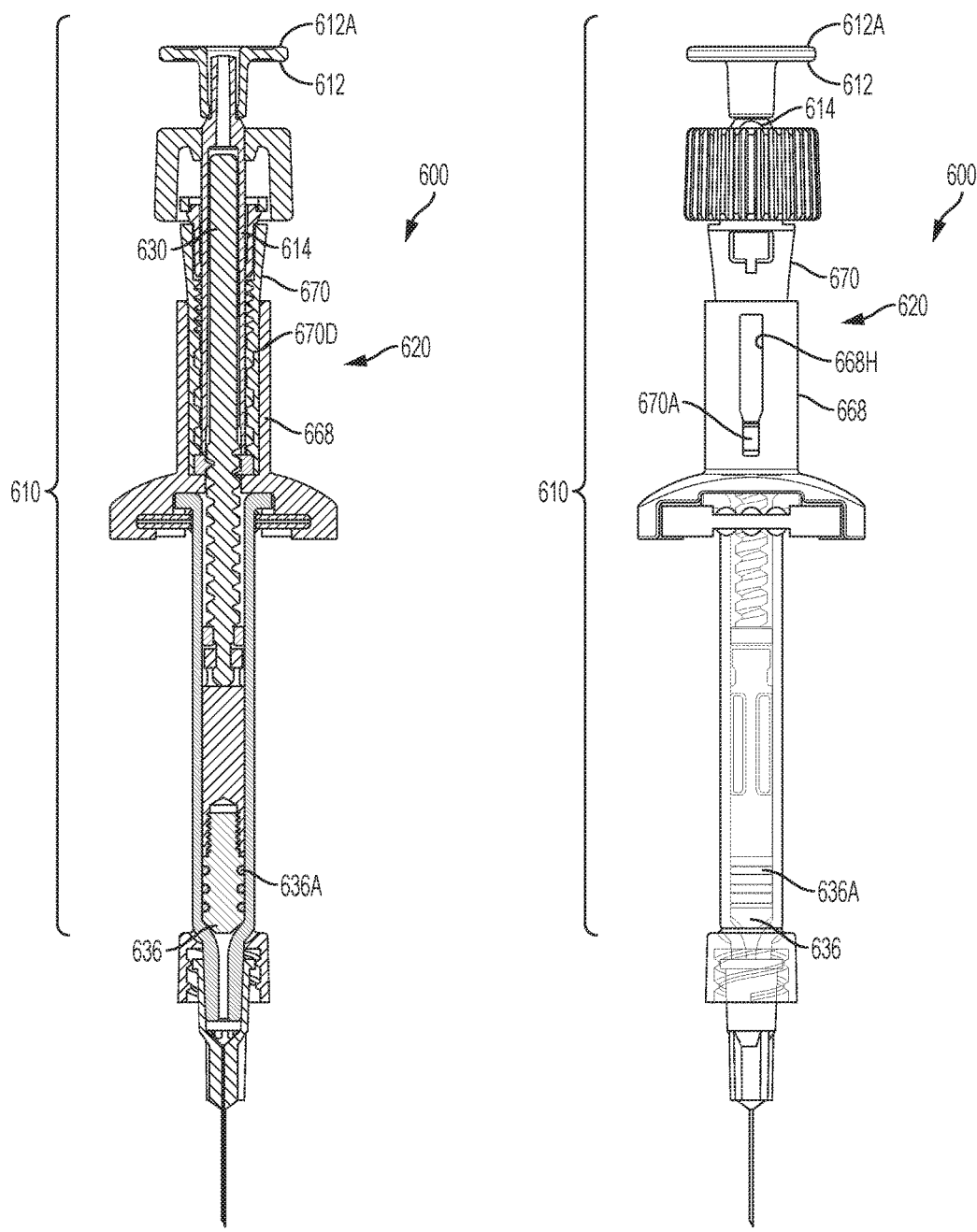
FIG. 10E is a cross-sectional view of the syringe of FIGS. 10A-10D at the completion of delivery.
FIG. 10F is a side elevational view of the syringe of FIGS. 10A-10D in the position illustrated in FIG. 10E.
Figure 12C:
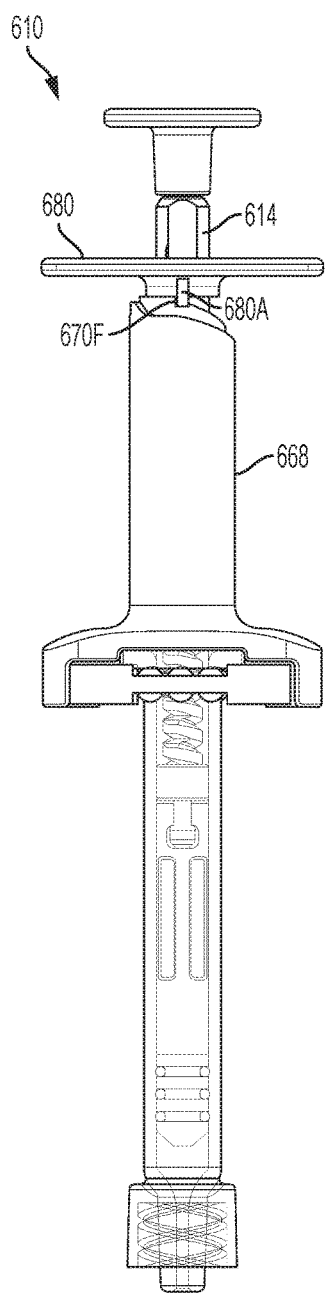
FIG. 12C is a side elevational view of the dose control mechanism of FIGS. 12A and 12B in a primed position.
Figure 12D:
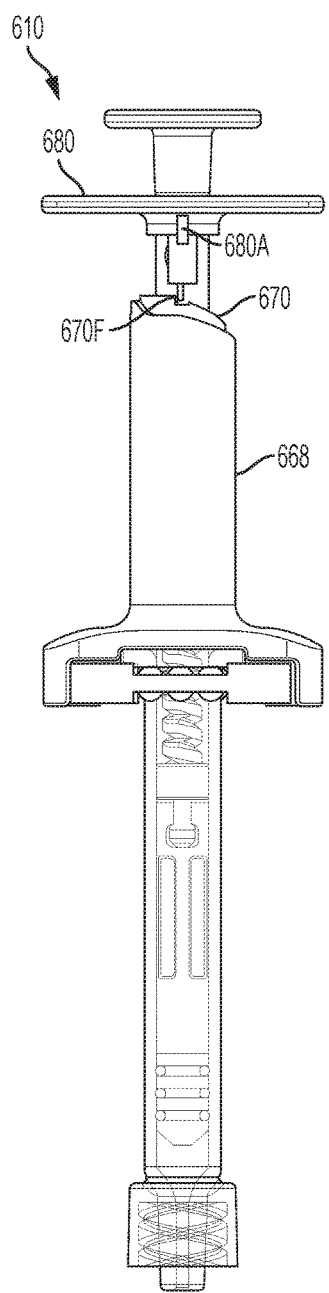
FIG. 12D is a side elevational view of the dose control mechanism of FIGS. 12A-12C in a ready position for delivery.
Figure 12E:
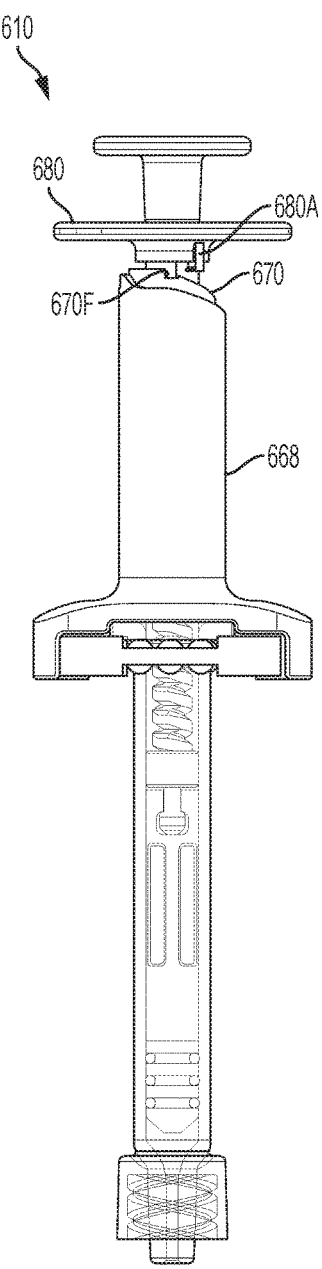
FIG. 12E is a side elevational view of the dose control mechanism of FIGS. 12A-12D during delivery.
Figure 13A:
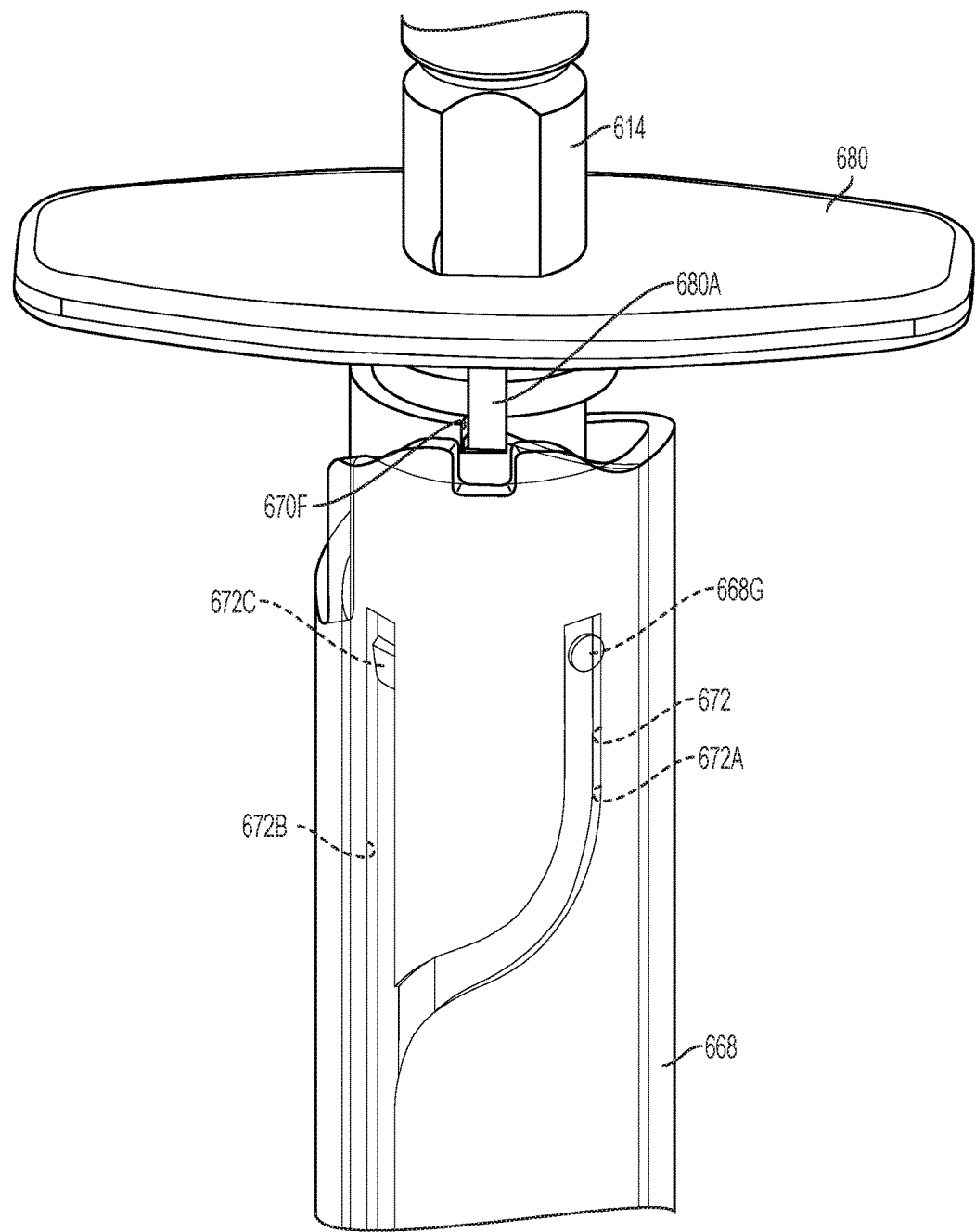
FIG. 13A is an enlarged fragmentary isometric view of the engaging aspects of the first and second housing sections of FIGS. 12A-12F in the retracted position illustrated in FIG. 12A, the first housing section being shown partially transparent to illustrate the internal structure.
Figure 13B:
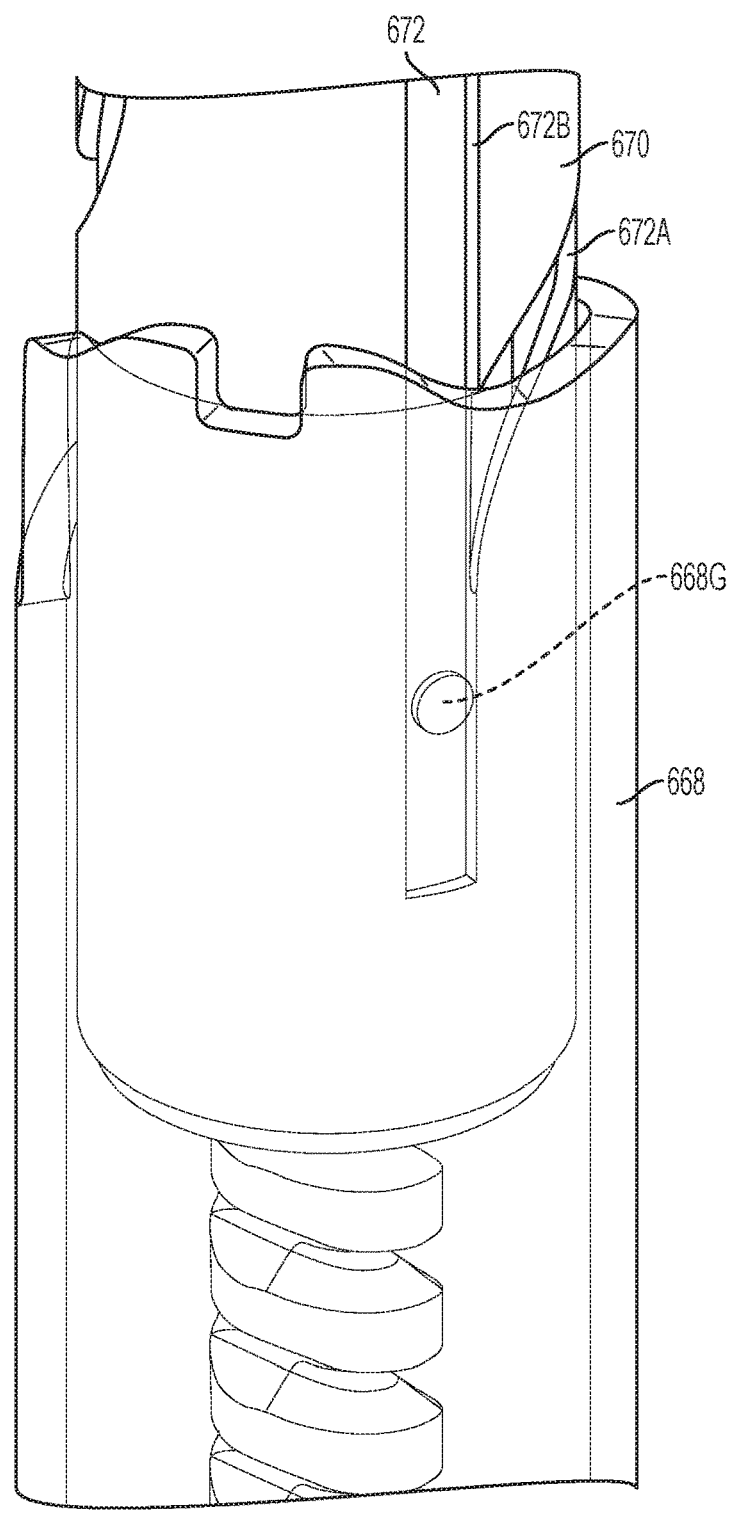
FIG. 13B is an enlarged fragmentary isometric view of the engaging aspects of the first and second housing sections of FIGS. 12A-12F in the extended position illustrated in FIG. 12B, the first housing section being shown partially transparent to illustrate the internal structure.
Figure 13C:
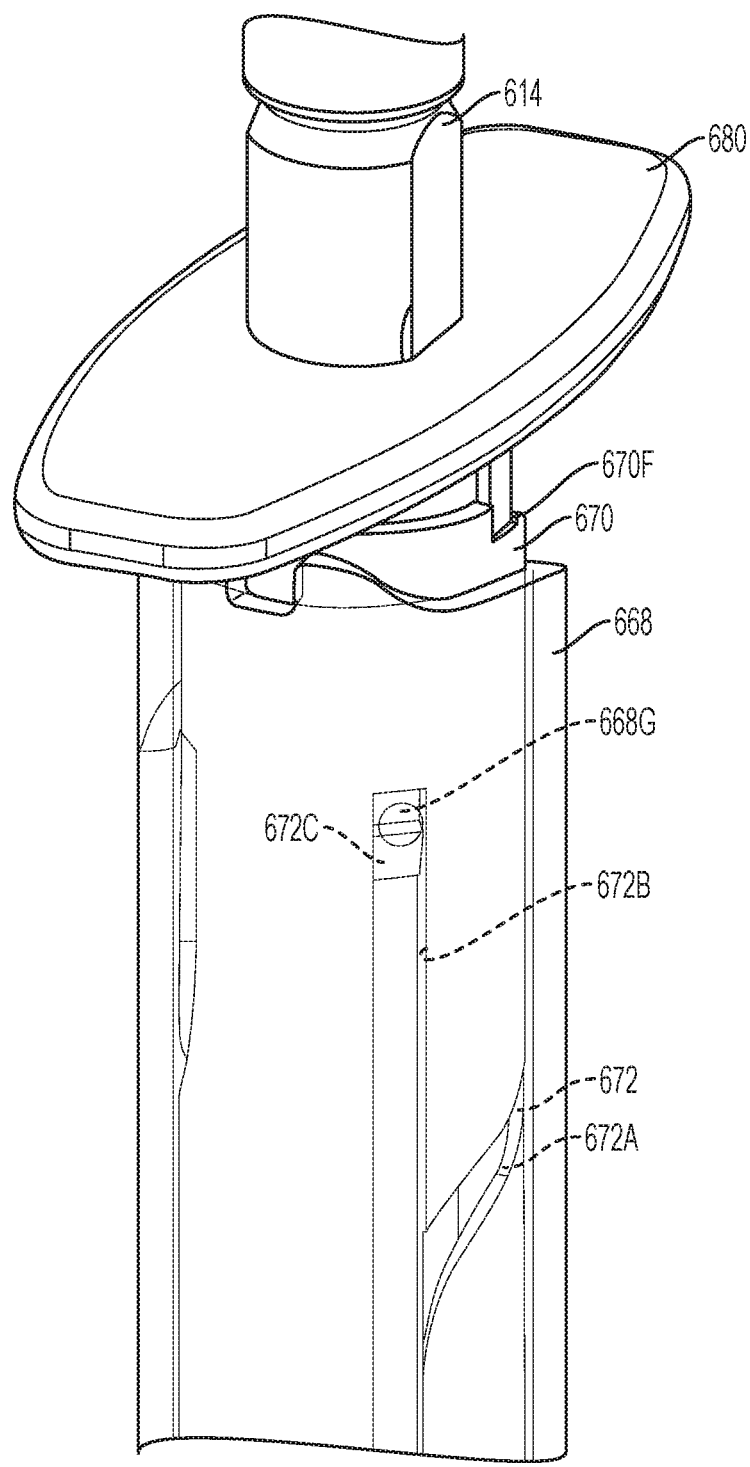
FIG. 13C is an enlarged fragmentary isometric view of the engaging aspects of the first and second housing sections of FIGS. 12A-12F in the delivery position illustrated in FIG. 12E, the first housing section being shown partially transparent to illustrate the internal structure.
Figure 14:
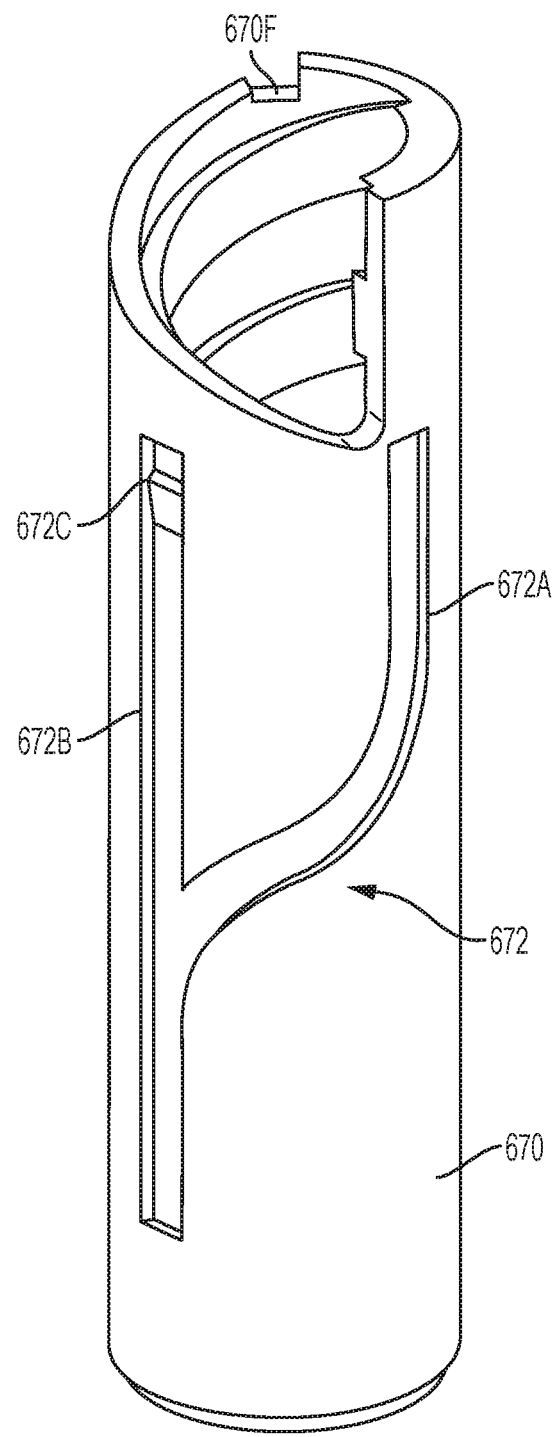
FIG. 14 is an enlarged isometric view of the second housing section of the embodiment of FIGS. 12A-13C.

To fill the syringe, the user pulls the button 612 in the proximal direction. This causes the plunger 614, second housing section 670, screw 630, plunger rod 634, and plunger seal 636 to translate in the proximal direction relative to the first housing section 668 from the retracted position illustrated in FIGS. 12A, and 13A, to the extended position illustrated in FIGS. 10A, 10B, 12B, 13B, thereby drawing fluid contents into the barrel of the syringe. After filling the syringe, the user may prime the syringe by depressing the button 612 in the distal direction. This causes the plunger 614, second housing section 670, screw 630, plunger rod 634, and plunger seal 636 to move as a unit and expel a portion of the fluid contained in the barrel (this position is shown in FIGS. 10C, 10D, and 12C). At the completion of this priming movement, the second housing section 670 engages the first housing section 668 such that the second housing section 670 cannot rotate or translate with respect to the first housing section 668. In this configuration, the dose control mechanism functions in like manner to the embodiment described above with reference to FIGS. 1A-7B.

FIGS. 10A-11B illustrate one embodiment of a locking mechanism to restrict relative movement of the second housing section 670 with respect to the first housing section 668. Second housing section 670 may include guide boss 670A and locking tab 670B. First housing section 668 may include longitudinal slot 668H. As can be seen in FIG. 10B, as second housing section 670 is translated proximally to fill the syringe, both guide boss 670A and locking tab 670B are disposed within longitudinal slot 668H. This restricts rotation of the second housing section 670 with respect to the first housing section 668. As can be seen in FIG. 10D, as second housing section 670 is translated in the distal direction, for example to prime the syringe, locking tab 670B has engaged first housing section 668 to restrict subsequent translation of the second housing section 670 with respect to first housing section 668. Additionally, or alternatively, interaction of guide boss 670A with longitudinal slot 668H may restrict distal translation of second housing section 670 with respect to first housing section 668.

In at least one embodiment, illustrated in FIGS. 12A-14, second housing section 670 has a track 672 which engages a guide aspect of the first housing section 668. Initially, the guide aspect 668G is disposed in first portion 672A of track 672, as seen in FIG. 13A. As the plunger 614, second housing section 670, screw 630, plunger rod 634, and plunger seal 636 are translated in the proximal direction from the retracted position of FIGS. 12A and 13A, the interaction of the guide aspect 668G and track 672 causes the second housing section 670 to rotate with respect to the first housing section 668 to the position shown in FIGS. 12B and 13B. That is, in addition to translating axially, the second housing section 670 rotates relative to the first housing section 668. Subsequently, distal translation of the second housing section 670 relative to the first housing section 668 results in the guide aspect 668G traversing the second portion 672B of the track 672 as the second housing section translates from the extended position illustrated in FIGS. 12B and 13B to the primed position shown in FIGS. 12C and 13C. The track 672 may include a locking aspect 672C which engages the guide aspect to restrict further translation of the second housing section 670 with respect to the first housing section 668.

During the steps of filling and priming, rotation of second housing section 670 and plunger 614 may be coupled to prevent relative rotation therebetween. For example, as shown in FIGS. 12A-14, dose control mechanism 610 may include coupler 680, which is in a keyed relationship with plunger 614. During the steps of filling and priming, tab 680A of coupler 680 may be disposed within notch 670F of second housing section 670, thereby restricting rotation of the second housing section 670 with respect to the coupler 680. Because of the keyed relationship of the coupler 680 and plunger 614, this engagement also prevents rotation of the second housing section 670 with respect to the plunger 614. The user may disengage the tab 680A of the coupler 680 from the notch 670F of the second housing section 670 by translating coupler 680 in the proximal direction (compare FIG. 12C and FIG. 12D). With the coupler 680 in this position, the dose control mechanism may be operated as described previously, the plunger 614 rotating relative to the housing 620 the tab 680A riding along an upper ramped surface of the housing 620, to rotate the screw 630 to expel the contents of the syringe barrel. The remaining elements of the dose control mechanism 610 of FIGS. 12A-14 are substantially as illustrated in FIGS. 10A-11B.

In any of the described embodiments, the dose control mechanism may include one or more additional threaded components. This may provide additional mechanical advantage to the user. For example, the dose control mechanism may include an inner plunger and an outer plunger. The outer plunger has an external thread engaging an internal thread of the housing and an internal thread engaging an external thread of the inner plunger. The inner plunger also has an internal thread engaging the screw. In this way, the ratio of displacement between the knob and the plunger seal may be increased.

According to yet another feature, some embodiments may provide tactile feedback to the user, for example, in connection with the identification of the desired delivery volume. In this way, when the user dials the plunger rod/screw to their desired dose volume (e.g., when the plunger 514 is rotated until a particular microliter setting is visible in the window 520A), the user will feel a tactile notch or stop-point to signal the positioning for a preset dose volume. The dose control mechanism 510 may be provided with multiple volume-based detents to indicate various dose volumes. By way of example only, the dose control mechanism 510 may include such feedback for syringe delivery volumes of 20 microliter, 10 microliter, and 5 microliter.

Figures 16A, 16B:
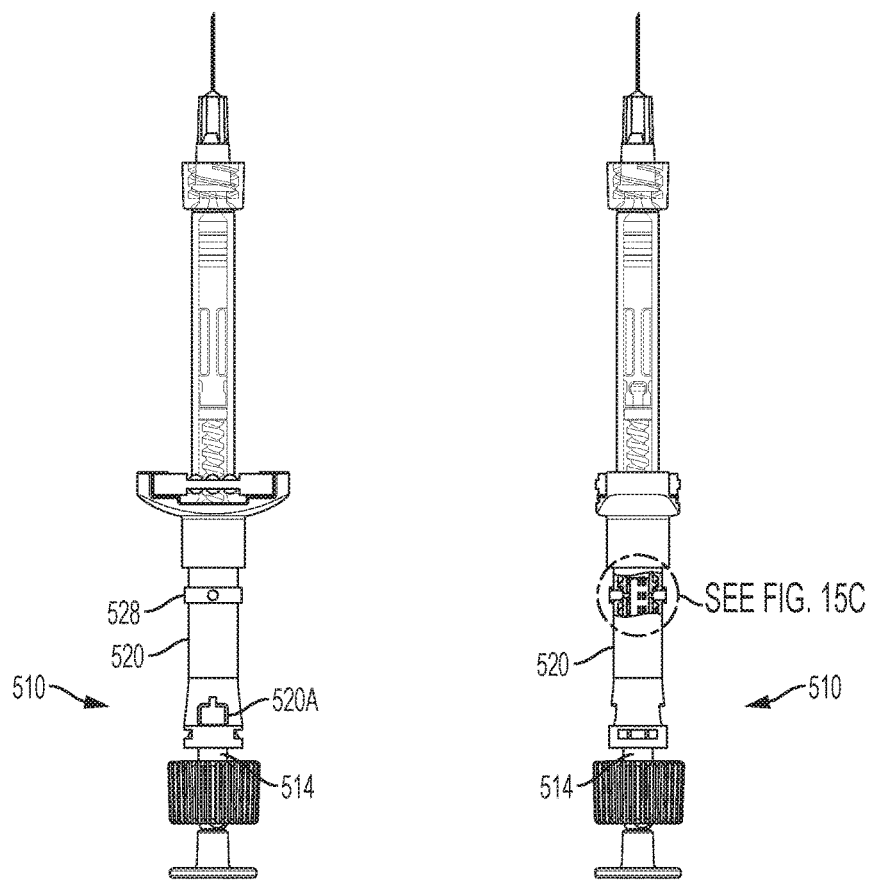
FIG. 16A is a side elevational view of a syringe incorporating a dose control mechanism according to another embodiment of the invention incorporating a tactile feedback feature.
FIG. 16B is a side elevational, partially cross-sectional view of the syringe of FIG. 16B partially broken away to illustrate the tactile feedback feature.
Figure 16C:
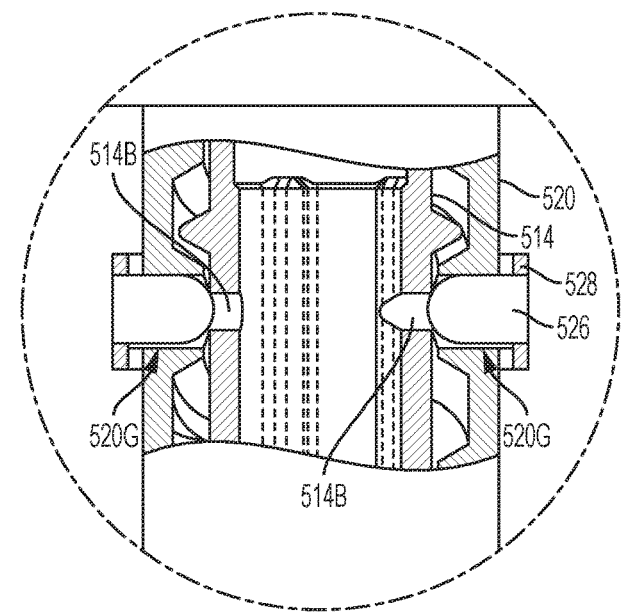
FIG. 16C is an enlarged view of the cross-sectioned portion of FIG. 16B.

While the tactile feedback may be provided by any appropriate arrangement, one such embodiment is illustrated in FIGS. 16A-16C. For example, the housing 520 and plunger 514 may include structures that, when aligned provide a tactile feedback. As most clearly shown in FIG. 16C, the housing 520 may include a protrusion 526 and the plunger 514 may include at least one recess 514B, which, when aligned, offer the user a variation in the normal rotation of the plunger 514.

The recess 514B in the plunger 514 may be formed by any appropriate method. For example, the recess 514B may be formed by a divot, or a bore extending through the wall of the plunger 514.

Similarly, the protrusion 526 may be provided by any appropriate structure, such as, a molded formation on the inner wall of the housing 520. In the illustrated embodiment, however, the housing 520 includes at least one radially extending aperture 520G through which a prong extends radially inward to provide the protrusion 526. In this embodiment, a pair of apertures 520G and a pair of protrusions 526 are provided. The protrusions 526 may extend from a separate clip 528 that may be attached to the outer surface of the housing 520, as illustrated in FIGS. 16A-C.

It will be appreciated that any number of such clips 528 may be provided, at locations along the length of housing 520, to identify a corresponding number of desired set-points/stop-points identifying preset dose volumes. Alternatively or additionally, the plunger 514 may be provided with any number of recesses 514B that correspond to preset dose volumes. As the user axially rotates the plunger rod/screw to dial their desired delivery volume, the protrusions 526 extending radially from the clip 528 are caused to contact/engage the recess 514B which corresponds to a defined set-point/stop-point. The recesses 514B and protrusions 526 are dimensioned such that each corresponds with a preset dose volume in the syringe for drug delivery.

Any of the dose control mechanisms described above can be used in conjunction with such a mixing syringe. Because the dose control mechanisms described herein allow for proximal translation of the plunger rod with respect to the drug container, they are particularly well-suited for such a mixing syringe.

Accordingly, the novel embodiments of the present invention provide dose control mechanisms, which allow for the accurate dosing and delivery of drug treatments, and drug delivery syringes which incorporate such control mechanisms. Such novel devices permit the identification and control of the dosage amount, permit the syringe to be "primed" (i.e., evacuated of air bubbles) prior to drug delivery, and ensure the accurate delivery of microliter volume dosages, all within a device size that is similar to commonly used conventional syringes available in the marketplace. Such novel devices are safe and easy to use, and are aesthetically and ergonomically appealing for clinical practitioners. The novel devices of the present invention provide these desirable features without any of the problems associated with known prior art devices.

A number of known filling processes and equipment may be utilized to achieve the filling steps of the syringe manufacturing process. The barrel assembly, needle, plunger seal, plunger rod, and other components described in these manufacturing and assembly processes may be as described above or may be a number of similar components which achieve the same functionality as these components. Throughout the specification, the aim has been to describe the preferred embodiments of the invention without limiting the invention to any one embodiment or specific collection of features. Various changes and modifications may be made to the embodiments described and illustrated without departing from the present invention. The disclosure of each patent and scientific document, computer program and algorithm referred to in this specification is incorporated by reference in its entirety.

What is claimed is:

1. A dose control mechanism for a syringe comprising:
a housing having a longitudinally extending channel having an interior surface;
an adapter including a channel having a fine pitch thread,
a plunger having an exterior surface and an axially extending channel, the axially extending channel including a first key aspect;
a screw having a screw exterior surface, a proximal end of the screw disposed at least partially within the axially extending channel of the plunger, the screw exterior surface including a second key aspect along a proximal portion of the screw exterior surface, at least a portion of the second key aspect disposed within the axially extending channel of the plunger and engaging the first key aspect for sliding movement such that rotational movement of the plunger causes rotational movement of the screw, a distal portion of the screw exterior surface including a fine pitch thread at least partially disposed within and interfacing with the fine pitch thread of the adapter; and
an engaging screw thread arrangement including at least one thread segment and a variable pitch thread, at least a portion of the longitudinally extending channel of the housing including one of the variable pitch thread and the at least one thread segment, the plunger including the other of the variable pitch thread and the at least one thread segment, the plunger residing at least partially within the housing with the at least one thread segment engaged with the variable pitch thread.

2. The dose control mechanism of claim 1, wherein the variable pitch thread includes a thread of at least two different pitches.

3. The dose control mechanism of claim 1, wherein the variable pitch thread includes at least one length of thread of a constant pitch.

4. The dose control mechanism of claim 1, wherein the housing includes the variable pitch thread and the variable pitch thread includes a distally-disposed coarse pitch thread and a proximally-disposed fine pitch thread.

5. The dose control mechanism of claim 4, wherein a pitch of the fine pitch thread of the variable pitch thread is substantially equal to a pitch of the fine pitch thread of the adapter.

6. The dose control mechanism of claim 5, wherein the housing includes at least a first housing section and a second housing section.

7. The dose control mechanism of claim 6, wherein the first housing section is an upper housing and the second housing section is a lower housing, the upper and lower housings being coupled together.

8. The dose control mechanism of claim 6, wherein the first housing section includes one of the coarse pitch thread and the fine pitch thread of the variable pitch thread and the second housing section includes the other of the coarse pitch thread and the fine pitch thread of the variable pitch thread.

9. The dose control mechanism of claim 1, whereby the engaging screw thread arrangement causes rotation of the plunger within the housing when the plunger is translated relative to at least a portion of the housing, rotation of the plunger within the housing provides rotation of the screw within the adapter channel, and rotation of the screw within the adapter channel and engagement of the first and second key aspects provides a relative axial sliding between the screw and the plunger and movement of the screw in a distal direction relative to the adapter when the plunger is depressed and in a proximal direction when the plunger is moved proximally relative to at least a portion of the housing.

10. The dose control mechanism of claim 1, wherein at least a portion of the variable pitch thread is of a coarser pitch than the fine pitch thread of the adapter.

11. The dose control mechanism of claim 1, further comprising one or more volume based detents.

12. The dose control mechanism of claim 11, wherein the one or more volume based detents comprise a protrusion configured to engage a recess of the plunger.

13. The dose control mechanism of claim 1, wherein the adapter is adapted to be coupled to a barrel of a syringe, and a distal end of the plunger is adapted to be coupled to a plunger rod disposed within the barrel.

14. A dose control mechanism for a syringe comprising:
a housing having a longitudinally extending channel having an interior surface, the housing including at least a first housing section and a second housing section disposed for telescoping movement relative to one another between a retracted position and an extended position;
an adapter including a channel having a fine pitch thread,
a plunger having an exterior surface and an axially extending channel, the axially extending channel including a first key aspect;
a screw having a screw exterior surface, a proximal end of the screw disposed at least partially within the axially extending channel of the plunger, the screw exterior surface including a second key aspect along a proximal portion of the screw exterior surface, at least a portion of the second key aspect disposed within the axially extending channel of the plunger and engaging the first key aspect for sliding movement such that rotational movement of the plunger causes rotational movement of the screw, a distal portion of the screw exterior surface including a fine pitch thread at least partially disposed within and interfacing with the fine pitch thread of the adapter; and
an engaging screw thread arrangement including at least one thread segment and a a thread, at least a portion of the longitudinally extending channel of the housing including one of the thread and the at least one thread segment, the plunger including the other of the thread and the at least one thread segment, the plunger residing at least partially within the housing with the at least one thread segment engaged with the thread.

15. The dose control mechanism of claim 14, wherein the first housing section and the second housing section are disposed for movement between the extended position and a primed position.

16. The dose control mechanism of claim 14, wherein the plunger and the first housing section are coupled to prevent rotational movement relative to one another during telescoping movement from the extended position.

17. The dose control mechanism of claim 14, wherein the first and second housing sections are disposed for controlled rotational movement relative to one another.

18. The dose control mechanism of claim 14, wherein the first and second housing sections are adapted to be coupled together in the primed position to prevent relative motion therebetween.

19. The dose control mechanism of claim 14, wherein the relative movement of the first and second housing sections between the retracted and extended positions is governed by at least one of the first and second housing sections including at least one guide aspect, and the other of the first and second housing sections including at least one track.

20. An accurate dose drug delivery syringe comprising a dose control mechanism of claim 1, a barrel, a plunger rod, a plunger seal coupled to the plunger rod and disposed within the barrel, and a needle, a proximal end of the plunger rod being coupled to a distal end of the screw and a distal end of the plunger rod being coupled to the plunger seal.

* * * * *